(12) United States Patent
Li et al.

(10) Patent No.: US 11,242,537 B2
(45) Date of Patent: Feb. 8, 2022

(54) METHOD FOR IMPROVING SENSITIVITY OF PLANT TO GIBBERELLIN INHIBITOR AND USE THEREOF

(71) Applicant: CHINA AGRICULTURAL UNIVERSITY, Beijing (CN)

(72) Inventors: Zhaohu Li, Beijing (CN); Juan Zhang, Beijing (CN); Fangjun Li, Beijing (CN); Mingcai Zhang, Beijing (CN); Mingwei Du, Beijing (CN); Xiaoli Tian, Beijing (CN); Liusheng Duan, Beijing (CN)

(73) Assignee: CHINA AGRICULTURAL UNIVERSITY, Beijing (CN)

( * ) Notice: Subject to any disclaimer, the term of this patent is extended or adjusted under 35 U.S.C. 154(b) by 0 days.

(21) Appl. No.: 16/480,794

(22) PCT Filed: Jan. 25, 2017

(86) PCT No.: PCT/CN2017/072607
§ 371 (c)(1),
(2) Date: Oct. 16, 2019

(87) PCT Pub. No.: WO2018/137173
PCT Pub. Date: Aug. 2, 2018

(65) Prior Publication Data
US 2021/0032648 A1  Feb. 4, 2021

(51) Int. Cl.
*C12N 15/82* (2006.01)
*C07K 14/415* (2006.01)

(52) U.S. Cl.
CPC ........ *C12N 15/8261* (2013.01); *C07K 14/415* (2013.01)

(58) Field of Classification Search
None
See application file for complete search history.

(56) References Cited

FOREIGN PATENT DOCUMENTS

CN  106367433 A  2/2017

OTHER PUBLICATIONS

Li et al. Access Nos. KJ00086 and A0A0F6P1E0; deposited Dec. 2013.*
NM_001327215.1, GenBank, Jan. 4, 2017, 1 page.
Li et al., "GhCPS and GhKS Encoding Gibberellin Biosynthesis Enzymes Involve in Inhibition of Leaf Growth by Mepiquat Chloride in Cotton (*Gossypium hirsutum* L.)," Acta Agronomica Sinica 2014, 40(8): 1350-1355, 6 pages, with English Abstract.
NM_001111859.2, GenBank, Jan. 2, 2016, 3 pages.
Harris et al., "The maize An2 gene is induced by Fusarium attack and encodes an ent-copalyl diphosphate synthase," Plant Molecular Biology (2005) 59:881-894, 14 pages.
International Search Report dated Oct. 31, 2017, issued in corresponding International Patent Application No. PCT/CN2017/072607.
Mudge, J. et al; KHG01750.1; GenBank; Ent-copalyl diphosphate synthase, chloroplastic [Gossypium arboreum]; Dec. 4, 2014; 2 pgs.
Verne, S. et al ; ABG79037.1; GenBank; GroES, partial [Wolbachia endosymbiont of Armadillidium vulgare]; Oct. 11, 2006; 1 pg.
Office Action issued in related Chinese Application No. 201510434881.2; dated Dec. 21, 2018; 11 pgs.
Office Action issued in related Chinese Application No. 201710056193.6; dated Mar. 6, 2020; 11 pgs.

* cited by examiner

*Primary Examiner* — Medina A Ibrahim
(74) *Attorney, Agent, or Firm* — Hauptman Ham, LLP

(57) ABSTRACT

The present invention discloses a method for increasing the sensitivity of a plant to a gibberellin inhibitor. The method for increasing the sensitivity of a plant to a gibberellin inhibitor provided by the present invention comprises the step of introducing an encoding gene of a protein into a recipient plant to obtain a transgenic plant; the transgenic plant has increased sensitivity to the gibberellin inhibitor compared to the recipient plant; the protein is a protein of the following a) or b) or c): a) a protein whose amino acid sequence is set forth in positions 1-821 of SEQ ID NO: 1; b) a protein whose amino acid sequence is set forth in SEQ ID NO: 1; c) a fusion protein obtained by attaching tag(s) to the N-terminus or/and C-terminus of a) or b). The experiments prove that the method for increasing the sensitivity of a plant to a gibberellin inhibitor of the present invention can be used to increase the sensitivity of plants to gibberellin inhibitors, and the plant height of plants can be regulated by the plant height-related protein HRP of the present invention.

14 Claims, 3 Drawing Sheets

Specification includes a Sequence Listing.

_US 11,242,537 B2_

SEQUENCE LISTING

<160> NUMBER OF SEQ ID NOS: 33

<210> SEQ ID NO 1
<211> LENGTH: 1062
<212> TYPE: PRT
<213> ORGANISM: G. arboreum

<400> SEQUENCE: 1

Met Phe Ser His Ser Phe Leu Ser Leu Pro Ser Ser Ser Pro Ser Ser

-continued

```
1               5                   10                  15
Ile Val Ser Phe Ser Asp Asn Gln Tyr His Pro Pro Leu Pro Phe Ala
            20                  25                  30
Gly Ile Trp Pro Leu Trp Gly Lys Asp Lys Gly Asp Asn Val Asp Ile
            35                  40                  45
Arg Pro Leu Cys Arg Ala Ile Ser Lys Pro Arg Thr Gln Glu Tyr Ala
50                  55                  60
Gly Val Phe Gln Asn Gly Leu Pro Val Ile Lys Trp Lys Glu Ile Val
65                  70                  75                  80
Asp Asp Asp Ile Glu Glu Gly Ala Leu Lys Val Tyr Glu Ser Asn
                85                  90                  95
Lys Val Lys Glu Arg Val Asp Thr Ile Lys Ser Met Leu Gly Ser Met
            100                 105                 110
Glu Asp Gly Glu Ile Ser Ser Ala Tyr Asp Thr Ala Trp Val Ala
            115                 120                 125
Leu Val Glu Asp Val Ser Gly Ser Gly Ala Pro Gln Phe Pro Ser Ser
130                 135                 140
Leu Glu Trp Ile Ala Asn Asn Gln Leu Pro Asp Gly Ser Trp Gly Asp
145                 150                 155                 160
Arg Gln Ile Phe Met Ala His Asp Arg Leu Ile Asn Thr Leu Ala Cys
                165                 170                 175
Val Ile Ala Leu Lys Thr Trp Gly Ile His Pro Asp Lys Cys Gln Lys
            180                 185                 190
Gly Val Ser Phe Phe Lys Asp Asn Ile Ser Lys Leu Glu Asn Glu Ser
            195                 200                 205
Glu Glu His Met Pro Ile Gly Phe Glu Val Ala Phe Pro Ser Leu Leu
210                 215                 220
Glu Ile Ala Arg Ser Leu His Ile Glu Val Pro Tyr Asp Ser Pro Val
225                 230                 235                 240
Phe Lys Asp Ile Tyr Ala Lys Arg Asp Leu Lys Leu Thr Arg Ile Pro
                245                 250                 255
Lys Glu Ile Met His Asn Val Pro Thr Thr Leu Leu His Ser Leu Glu
            260                 265                 270
Gly Met Pro Asp Leu Asp Trp Glu Lys Leu Leu Lys Leu Gln Cys Ile
            275                 280                 285
Asp Gly Ser Phe Leu Phe Ser Pro Ser Ser Thr Ala Phe Ala Leu Met
290                 295                 300
Gln Thr Lys Gly Glu Asn Cys Leu Arg Tyr Leu Met Lys Thr Val Gln
305                 310                 315                 320
Arg Phe Asn Gly Gly Val Pro Asn Val Tyr Pro Val Asp Leu Phe Glu
                325                 330                 335
His Ile Trp Thr Val Asp Arg Leu Gln Arg Leu Gly Ile Ser Arg Tyr
            340                 345                 350
Phe His Pro Glu Ile Lys Glu Cys Leu Asp Tyr Val Tyr Arg Tyr Trp
            355                 360                 365
Thr Glu Asp Gly Ile Ser Trp Ala Arg Asn Thr Arg Val Tyr Asp Ile
            370                 375                 380
Asp Asp Thr Ala Met Gly Phe Arg Leu Leu Arg Val His Gly Tyr Glu
385                 390                 395                 400
Val Ser Ser Asp Val Phe Arg His Phe Glu Lys Gly Gly Glu Phe Phe
                405                 410                 415
Cys Phe Val Gly Gln Ser Asn Gln Ala Ile Thr Gly Ile Phe Asn Leu
            420                 425                 430
```

```
Tyr Arg Ala Ser Gln Val Leu Phe Pro Gly Glu Lys Ile Leu Glu Asp
        435                 440                 445

Ala Lys Arg Phe Ser Ser Lys Phe Leu Thr Gln Lys Gln Ala Ala Asp
450                 455                 460

Glu Leu Leu Asp Lys Trp Ile Ile Thr Lys Asp Leu Pro Gly Glu Val
465                 470                 475                 480

Gly Leu Ala Leu Asn Leu Pro Trp Tyr Ala Ser Leu Pro Arg Val Glu
                485                 490                 495

Thr Arg Phe Tyr Ile Glu Gln Tyr Gly Glu Asp Asp Val Trp Ile
                500                 505                 510

Gly Lys Thr Leu Tyr Arg Met Arg Tyr Val Asn Asn Val Phe Leu
        515                 520                 525

Asp Leu Ala Lys Gln Asp Tyr Asn Asn Cys Gln Ala Leu His Arg Met
530                 535                 540

Glu Trp Asp Ser Met Gln Lys Trp Tyr Ser Glu Met Gly Leu Ala Asp
545                 550                 555                 560

Phe Gly Val Thr Arg Arg Ser Leu Leu Leu Thr Tyr Phe Met Ala Ala
                565                 570                 575

Ala Ser Ile Phe Glu Leu Glu Arg Ser Gln Glu Arg Leu Ala Trp Ala
        580                 585                 590

Lys Thr Ala Phe Leu Val Asp Thr Ile Ser Ser Phe Asp Asn Ala
        595                 600                 605

Arg Lys Pro Lys Asp Leu Arg Asn Ser Phe Leu Leu Val Phe Arg Thr
        610                 615                 620

Val Val Asp Ala Arg Phe Gly His Ile Asn Ala Arg Lys Leu Asp Ser
625                 630                 635                 640

Asn Arg Thr Ile Gln Lys Met Ile Asp Ile Leu Leu Arg Thr Leu Asn
                645                 650                 655

His Leu Ser Leu Asp Ala Leu Val Ala His Gly Arg Asp Ile Ser Cys
                660                 665                 670

Ser Ile Arg Arg Ala Trp Glu Lys Trp Met Leu Met Trp Val Glu Asp
        675                 680                 685

Gly Asp Arg His Arg Gly Leu Ala Glu Leu Val Val Gln Thr Ile Asn
        690                 695                 700

Leu Ser Ser Gly Arg Trp Ser Leu Asp Glu Leu Leu Ser His Pro Arg
705                 710                 715                 720

Tyr Asp Pro Leu Ser Ser Leu Thr Asn Ser Val Cys His Gln Leu Tyr
                725                 730                 735

His Arg Gln Met Leu Lys Val His Val Asn Gly Cys Tyr Asn Asn Glu
                740                 745                 750

Thr Glu Asn Asn Ile Thr Arg Glu Ile Asp Ser Asn Met Gln Glu Leu
        755                 760                 765

Val Gln Leu Val Leu Gln Asn Pro Ser Ala Ala Asp Gln Asn Ser
770                 775                 780

Glu Phe Arg Gln Thr Phe Leu Thr Val Ala Arg Ser Phe Tyr Tyr Ala
785                 790                 795                 800

Ala His Cys Asp Leu Asp Thr Ile Thr Phe His Ile Ala Lys Val Leu
                805                 810                 815

Phe Glu Lys Val Arg Gly Thr Met Val Ser Lys Gly Glu Glu Leu Phe
                820                 825                 830

Thr Gly Val Val Pro Ile Leu Val Glu Leu Asp Gly Asp Val Asn Gly
                835                 840                 845
```

His Lys Phe Ser Val Ser Gly Glu Gly Glu Gly Asp Ala Thr Tyr Gly
850             855             860

Lys Leu Thr Leu Lys Phe Ile Cys Thr Thr Gly Lys Leu Pro Val Pro
865             870             875             880

Trp Pro Thr Leu Val Thr Thr Leu Thr Tyr Gly Val Gln Cys Phe Ser
                885             890             895

Arg Tyr Pro Asp His Met Lys Gln His Asp Phe Phe Lys Ser Ala Met
            900             905             910

Pro Glu Gly Tyr Val Gln Glu Arg Thr Ile Phe Phe Lys Asp Asp Gly
        915             920             925

Asn Tyr Lys Thr Arg Ala Glu Val Lys Phe Glu Gly Asp Thr Leu Val
        930             935             940

Asn Arg Ile Glu Leu Lys Gly Ile Asp Phe Lys Glu Asp Gly Asn Ile
945             950             955             960

Leu Gly His Lys Leu Glu Tyr Asn Tyr Asn Ser His Asn Val Tyr Ile
                965             970             975

Met Ala Asp Lys Gln Lys Asn Gly Ile Lys Val Asn Phe Lys Ile Arg
            980             985             990

His Asn Ile Glu Asp Gly Ser Val Gln Leu Ala Asp His Tyr Gln Gln
            995             1000            1005

Asn Thr Pro Ile Gly Asp Gly Pro Val Leu Leu Pro Asp Asn His
    1010            1015            1020

Tyr Leu Ser Thr Gln Ser Ala Leu Ser Lys Asp Pro Asn Glu Lys
    1025            1030            1035

Arg Asp His Met Val Leu Leu Glu Phe Val Thr Ala Ala Gly Ile
    1040            1045            1050

Thr Leu Gly Met Asp Glu Leu Tyr Lys
    1055            1060

<210> SEQ ID NO 2
<211> LENGTH: 3195
<212> TYPE: DNA
<213> ORGANISM: G. arboreum

<400> SEQUENCE: 2
atgttttccc attccttcct ctccctcccc tcctcctctc cttcttctat agtttccttc      60
tccgataatc aatatcatcc tcccttaccc tttgcaggca tttggccgtt atggggtaaa     120
gacaaaggcg ataacgttga tattcggccc ttatgcagag ctatatccaa accccgcact     180
caagaatatg ctggcgtgtt tcaaaatggt ctgccagtta taagtggaa ggagattgtg      240 gatgatgaca tagaagaaga gggagctctt aaggtttatg agtcgaataa ggtaaaggaa     300
cgtgtggaca ccattaagtc gatgctgggt tccatggagg atggagagat aagtagctca     360
gcttatgaca cagcctgggt tgctctggtt gaagacgtta gcggtagcgg tgctcctcag     420
tttccatcca gcctcgaatg gatcgctaac aatcagctcc ccgatggatc ctggggcgat     480
agacaaatat tcatggcaca tgatcgtctg atcaacactt tagcttgtgt tattgccttg     540
aaaacatggg gtattcatcc tgacaaatgc agaaaggggt gtcgtttttt caaagataat     600
ataagcaaac tcgaaaacga gagtgaggag cacatgccaa tcgggtttga agtggctttt     660
ccttcgcttc tggagatagc tcgaagttta cacattgaag taccgtatga ctcccctgtc     720
tttaaagaca tctatgcaaa gagagatcta aagctcacaa ggataccaaa ggagataatg     780
cataatgtac ccacaacact actccatagc cttgaaggga tgccagactt ggactgggaa     840
aagcttttga agttgcagtg catagatggg tctttcttgt tctcgccatc ctccactgcc     900

```
ttcgcactca tgcaaaccaa aggtgagaat tgcctcagat atttaatgaa aactgttcaa      960
agattcaatg ggggagtccc caatgtgtat ccggttgacc tgtttgaaca tatttggact     1020
gtcgaccgct tgcaacgcct tgggatttca agatatttcc acccagaaat taaagaatgc     1080
ctagattacg tttatagata ctggactgaa gatggaattt cctgggcaag aaacactcgg     1140
gtttatgaca ttgacgacac ggccatgggg tttaggttac taagggtaca tggatacgag     1200
gtttcttcag atgtgttccg acattttgag aaaggcgggg agttcttctg ctttgtgggg     1260
cagtccaacc aagccataac cgggattttc aacctgtata gggcttccca ggtgctgttc     1320
cctggagaaa agattcttga ggatgccaag cgcttttcat ccaaattttt aacacaaaaa     1380
caagcggctg atgaattatt agacaaatgg atcattacca aagacttacc tggtgaggtt     1440
gggttggcat tgaatctccc atggtatgca agcctgccta gagttgaaac aaggttttac     1500
atagaacaat atggaggtga agatgatgtg tggattggaa aaactcttta caggatgcgg     1560
tatgtgaaca ataatgtgtt ccttgatctt gcaaaacaag actacaataa ttgccaagct     1620
ttgcatagga tggaatggga tagtatgcaa aagtggtact cggaaatggg tctggctgat     1680
tttggggtga cccgtagatc tcttctctta acttatttta tggcggcagc cagcatattc     1740
gagcttgaaa ggtcgcaaga gcggctggct tgggctaaga ccgcttttct ggtcgacacc     1800
atctcctctt cttttgacaa tgcaaggaaa cctaaggacc ttaggaattc tttcctccta     1860
gtcttcagaa ctgttgttga tgcacgattt ggccacatta atgcgaggaa gttggactca     1920
aacaggacaa ttcagaagat gatagacatc ttgcttcgga ccctgaacca tctatcattg     1980
gacgcacttg tggctcatgg tcgagacatt agctgcagca ttcgccgtgc ttgggaaaag     2040
tggatgctga tgtgggtgga ggatggtgat aggcaccgag gactcgcaga gttagtggtg     2100
cagaccatca acctcagctc tggccgttgg tccttggacg aactgttgtc tcatccccga     2160
tacgacccac tctccagcct cacaaattca gtttgccatc agctttatca tcgccaaatg     2220
ctaaaggtgc acgtcaatgg ctgctacaat aatgaaacag agaacaacat aacccgggaa     2280
atagattcca acatgcaaga gctcgttcag ttagtactgc aaaatccctc ggccgctgat     2340
gaccaaaact cagaattcag gcaaacattt cttacggtgg cacggagttt ttactatgct     2400
gcacactgtg acttagacac catcacattt catattgcta agtactctt tgagaaagta     2460
cgcggtacca tggtgagcaa gggcgaggag ctgttcaccg gggtggtgcc catcctggtc     2520
gagctggacg gcgacgtaaa cggccacaag ttcagcgtgt ccggcgaggg cgagggcgat     2580
gccacctacg gcaagctgac cctgaagttc atctgcacca ccggcaagct gcccgtgccc     2640
tggcccaccc tcgtgaccac cctgacctac ggcgtgcagt gcttcagccg ctaccccgac     2700
cacatgaagc agcacgactt cttcaagtcc gccatgcccg aaggctacgt ccaggagcgc     2760
accatcttct tcaaggacga cggcaactac aagacccgcg ccgaggtgaa gttcgagggc     2820
gacaccctgg tgaaccgcat cgagctgaag ggcatcgact tcaaggagga cggcaacatc     2880
ctggggcaca agctggagta caactacaac agccacaacg tctatatcat ggccgacaag     2940
cagaagaacg gcatcaaggt gaacttcaag atccgccaca acatcgagga cggcagcgtg     3000
cagctcgccg accactacca gcagaacacc cccatcggcg acggccccgt gctgctgccc     3060
gacaaccact acctgagcac ccagtccgcc ctgagcaaag accccaacga gaagcgcgat     3120
cacatggtcc tgctggagtt cgtgaccgcc gccgggatca ctctcggcat ggacgagctg     3180
tacaagtaag agctc                                                      3195
```

<210> SEQ ID NO 3
<211> LENGTH: 2565
<212> TYPE: DNA
<213> ORGANISM: Artificial Sequence
<220> FEATURE:
<223> OTHER INFORMATION: Synthesized

<400> SEQUENCE: 3

| | | | | | |
|---|---|---|---|---|---|
| atgaagctcc | tctcgccggc | ggccgcaccg | tcgtcctcgc | cgttgttccc | tcctcgcatc | 60 |
| gtcgaagctg | cagctcgtca | atcaggtcca | tgccgtatcc | gcatccgtat | ccgtggcaaa | 120 |
| gcagcagcag | caggaggagg | aggaggcgcg | ggcgcgacgg | ggccccgcgg | cagcctcagg | 180 |
| ctcgccgggt | ggtggagagc | gcagcagcag | gccccggcca | cggcgacgac | aacgcagcag | 240 |
| cctgacaacg | tctccagtgc | taaagtgttc | cagaccagcc | gtgtggaaac | cgagtccgaa | 300 |
| attgcgaaat | ggccagggaa | accacaagac | cttgaggatg | agcaccaggc | tgaggaggca | 360 |
| gagctgcagc | cacttatcga | ccaggtgagg | gcgatgctac | ggtcgatgaa | cgacggggat | 420 |
| accagcgcct | cggcgtacga | cacggcgtgg | gtggcgatgg | tgccgaaggt | gggcggcgac | 480 |
| ggcggcgccc | agccccagtt | cccggccacc | gtgcgctgga | tcgtggacca | ccagctgccc | 540 |
| gacggctcct | ggggcgactc | ggccctgttc | tccgcctacg | accgcatgat | caacaccctc | 600 |
| gcctgcgtcg | tcgcgctgac | caagtggtcg | ctggagcccg | cgaggtgcga | ggcggggctc | 660 |
| tcgttcctgc | acgagaacat | gtggaggcta | gcggaggagg | aggcggagtc | gatgcccatc | 720 |
| ggcttcgaga | tcgccttccc | ttctctcatc | cagacggcta | gggacctggg | cgtcgtcgac | 780 |
| ttcccgtacg | acacccggc | gctgcagagc | atatacgcca | acaggaagt | caagctgaag | 840 |
| cggatcccaa | gggacatgat | gcacagggtc | ccgacgtcca | tcctgcacag | ccttgaaggg | 900 |
| atgcctgacc | tggactggcc | gaggcttctg | aacctccagt | cctgcgacgg | ctccttcttg | 960 |
| ttctctcctt | cggctaccgc | ttacgcgctg | atgcaaaccg | gtgacaagaa | gtgcttcgaa | 1020 |
| tacatcgaca | ggattgtcaa | aaaattcaac | ggggagtcc | ccaatgttta | tccggtcgat | 1080 |
| cttttcgagc | acatctgggt | tgtggatcgg | ttggagcgac | tcgggatctc | ccgctacttc | 1140 |
| caacgagaga | ttgagcagtg | catggactat | gtgaacaggc | actggactga | agatgggatt | 1200 |
| tgctggcta | ggaaatccaa | tgtgaaggat | gtggatgaca | cagctatggc | tttccgacta | 1260 |
| ctaaggctac | atggatacaa | tgtctctcca | agtgtgttta | agaactttga | gaaagatgga | 1320 |
| gagttctttt | gttttgtggg | ccaatcgact | caagccgtca | ctgggatgta | aacctcaac | 1380 |
| agagcctctc | agataagttt | tcaaggagag | gatgtattgc | atcgtgctag | gttttctcg | 1440 |
| tatgagtttc | tgagacagag | agaagaacaa | ggcatgatcc | gtgataaatg | gatcgttgcc | 1500 |
| aaggatctac | ctggcgaggt | gcaatataca | ctagacttcc | cttggtatgc | aagcttgcct | 1560 |
| cgtgtagagg | caagaaccta | tctagatcaa | tatggtggta | aagatgacgt | ttggattgga | 1620 |
| aagacactct | acaggatgcc | tcttgtgaat | aacgacacat | atctagagtt | ggcaataagg | 1680 |
| gatttcaacc | attgccaagc | tctgcatcag | cttgagtgta | atgggctgca | aacgtggtac | 1740 |
| aaggataatt | gccttgacgc | ttttggagta | gaaccacaag | atgttttaag | atcttacttt | 1800 |
| ttagctgctg | cttgcatttt | tgaacctagc | cgtgctgctg | agcggcttgc | atgggctaga | 1860 |
| acgtcaatga | ttgccaatgc | catttctaca | catcttcgtg | acatttcgga | agacaagaag | 1920 |
| agattggaat | gtttcgtgca | ctgtctctat | gaagaaaacg | atgtatcatg | gcttaaacga | 1980 |
| aatcctaatg | atgttattct | tgagagggca | cttcgaagat | taattaactt | attagcacaa | 2040 |
| gaagcattgc | caattcatga | aggacaaaga | ttcatacaca | gtctattgag | tcttgcatgg | 2100 |

| | |
|---|---|
| accgaatgga tgttgcaaaa ggcaaataaa gaagaaaaca aatatcacaa atgcagtggt | 2160 |
| atagaaccac aatacatggt tcatgatagg caaacatact tactttagt tcaggttatt | 2220 |
| gagatttgtg ctggacgaat tggtgaggct gtgtcaatga taaacaacaa ggataatgat | 2280 |
| tggtttattc aactcacatg tgctacttgt gacagtctta accataggat gttactgtcc | 2340 |
| caggatacta tgaagaatga agcaagaata aattggattg agaaggaaat cgagttgaat | 2400 |
| atgcaagagc ttgctcaatc tctccttttg agatgtgatg agaaaactag caataagaag | 2460 |
| accaagaaaa ccttatggga tgtcctaaga agtttatact atgctactca ttccccacaa | 2520 |
| catatgatcg atagacatgt ttccagagtt atctttgagc ctgtt | 2565 |

<210> SEQ ID NO 4
<211> LENGTH: 2566
<212> TYPE: DNA
<213> ORGANISM: Zea mays

<400> SEQUENCE: 4

| | |
|---|---|
| atgaagctcc tctcgccggc ggccgcaccg tcgtcctcgc cgttgttccc tcctcgcatc | 60 |
| gtcgaagctg cagctcgtca atcaggtcca tgccgtatcc gcatccgtat ccgtggcaaa | 120 |
| gcagcagcag caggaggagg aggaggcgcg ggcgcgacgg ggccccgcgg cagcctcagg | 180 |
| ctcgccgggt ggtggagagc gcagcagcag gccccggcca cggcgacgac aacgcagcag | 240 |
| cctgacaacg tctccagtgc taaagtgttc cagaccagcc gtgtggaaac cgagtccgaa | 300 |
| attgcgaaat ggccagggaa accacaagta gcgggagatc ccgagtgctg aggaggcaga | 360 |
| gctgcagcca cttatcgacc aggtgagggc gatgctacgg tcgatgaacg acggggatac | 420 |
| cagcgcctcg gcgtacgaca cggcgtgggt ggcgatggtg ccgaaggtgg gcggcgacgg | 480 |
| cggcgcccag ccccagttcc cggccaccgt gcgctggatc gtggaccacc agctgcccga | 540 |
| cggctcctgg ggcgactcgg ccctgttctc cgcctacgac cgcatgatca cacccctcgc | 600 |
| ctgcgtcgtc gcgctgacca gtggtcgct ggagcccgcg aggtgcgagg cggggctctc | 660 |
| gttcctgcac gagaacatgt ggaggctagc ggaggaggag gcggagtcga tgcccatcgg | 720 |
| cttcgagatc gccttccctt ctctcatcca cggctagg gacctgggcg tcgtcgactt | 780 |
| cccgtacgga cacccggcgc tgcagagcat atacgccaac agggaagtca agctgaagcg | 840 |
| gatcccaagg gacatgatgc acagggtccc gacgtccatc ctgcacagcc ttgaagggat | 900 |
| gcctgacctg gactggccga ggcttctgaa cctccagtcc tgcgacggct ccttcttgtt | 960 |
| ctctccttcg gctaccgctt acgcgctgat gcaaaccggt gacaagaagt gcttcgaata | 1020 |
| catcgacagg attgtcaaaa aattcaacgg gggagtcccc aatgtttatc cggtcgatct | 1080 |
| tttcgagcac atctgggttg tggatcggtt ggagcgactc gggatctccc gctacttcca | 1140 |
| acgagagatt gagcagtgca tggactatgt gaacaggcac tggactgaag atgggatttg | 1200 |
| ctgggctagg aaatccaatg tgaaggatgt ggatgacaca gctatggctt ccgactact | 1260 |
| aaggctacat ggatacaatg tctctccaag tgtgtttaag aactttgaga agatggaga | 1320 |
| gttcttttgt tttgtgggcc aatcgactca agccgtcact gggatgtata acctcaacag | 1380 |
| agcctctcag ataagttttc aaggagagga tgtattgcat cgtgctaggg ttttctcgta | 1440 |
| tgagtttctg agacagagag aagaacaagg catgatccgt gataaatgga tcgttgccaa | 1500 |
| ggatctacct ggcgaggtgc aatatacact agacttccct tggtatgcaa gcttgcctcg | 1560 |
| tgtagaggca agaacctatc tagatcaata tggtggtaaa gatgacgttt ggattggaaa | 1620 |

```
gacactctac aggatgcctc ttgtgaataa cgacacatat ctagagttgg caataaggga    1680
tttcaaccat tgccaagctc tgcatcagct tgagtgtaat gggctgcaaa cgtggtacaa    1740
ggataattgc cttgacgctt ttggagtaga accacaagat gttttaagat cttactttt    1800 agctgctgct tgcatttttg aacctagccg tgctgctgag cggcttgcat gggctagaac    1860
gtcaatgatt gccaatgcca tttctacaca tcttcgtgac atttcggaag acaagaagag    1920
attggaatgt ttcgtgcact gtctctatga agaaaacgat gtatcatggc ttaaacgaaa    1980
tcctaatgat gttattcttg agagggcact tcgaagatta attaacttat tagcacaaga    2040
agcattgcca attcatgaag gacaaagatt catacacagt ctattgagtc ttgcatggac    2100
cgaatggatg ttgcaaaagg caaataaaga agaaaacaaa tatcacaaat gcagtggtat    2160
agaaccacaa tacatggttc atgataggca aacatactta cttttagttc aggttattga    2220
gatttgtgct ggacgaattg gtgaggctgt gtcaatgata aacaacaagg ataatgattg    2280
gtttattcaa ctcacatgtg ctacttgtga cagtcttaac cataggatgt tactgtccca    2340
ggatactatg aagaatgaag caagaataaa ttggattgag aaggaaatcg agttgaatat    2400
gcaagagctt gctcaatctc tccttttgag atgtgatgag aaaactagca ataagaagac    2460
caagaaaacc ttatgggatg tcctaagaag tttatactat gctactcatt ccccacaaca    2520
tatgatcgat agacatgttt ccagagttat ctttgagcct gtttaa                  2566

<210> SEQ ID NO 5
<211> LENGTH: 20
<212> TYPE: DNA
<213> ORGANISM: Artificial Sequence
<220> FEATURE:
<223> OTHER INFORMATION: Synthesized

<400> SEQUENCE: 5
accgaggact cgcagagtta                                                  20

<210> SEQ ID NO 6
<211> LENGTH: 20
<212> TYPE: DNA
<213> ORGANISM: Artificial Sequence
<220> FEATURE:
<223> OTHER INFORMATION: Synthesized

<400> SEQUENCE: 6 accttagca tttggcgatg                                                   20

<210> SEQ ID NO 7
<211> LENGTH: 20
<212> TYPE: DNA
<213> ORGANISM: Artificial Sequence
<220> FEATURE:
<223> OTHER INFORMATION: Synthesized

<400> SEQUENCE: 7
tgcagccact tatcgaccag                                                  20

<210> SEQ ID NO 8
<211> LENGTH: 20
<212> TYPE: DNA
<213> ORGANISM: Artificial Sequence
<220> FEATURE:
<223> OTHER INFORMATION: Synthesized

<400> SEQUENCE: 8
aggcgagggt gttgatcatg                                                  20
```

```
<210> SEQ ID NO 9
<211> LENGTH: 20
<212> TYPE: DNA
<213> ORGANISM: Artificial Sequence
<220> FEATURE:
<223> OTHER INFORMATION: Synthesized

<400> SEQUENCE: 9
attacccgat gggcaagtca                                              20

<210> SEQ ID NO 10
<211> LENGTH: 20
<212> TYPE: DNA
<213> ORGANISM: Artificial Sequence
<220> FEATURE:
<223> OTHER INFORMATION: Synthesized

<400> SEQUENCE: 10
cacaaacgag ggctggaaca                                              20

<210> SEQ ID NO 11
<211> LENGTH: 19
<212> TYPE: DNA
<213> ORGANISM: Artificial Sequence
<220> FEATURE:
<223> OTHER INFORMATION: Synthesized

<400> SEQUENCE: 11
agctgaagcg gatcccaag                                               19

<210> SEQ ID NO 12
<211> LENGTH: 38
<212> TYPE: DNA
<213> ORGANISM: Artificial Sequence
<220> FEATURE:
<223> OTHER INFORMATION: Synthesized

<400> SEQUENCE: 12
atatatggtc tctggcgaaa ttgcgaaatg gccaggtt                          38

<210> SEQ ID NO 13
<211> LENGTH: 40
<212> TYPE: DNA
<213> ORGANISM: Artificial Sequence
<220> FEATURE:
<223> OTHER INFORMATION: Synthesized

<400> SEQUENCE: 13
tgaaattgcg aaatggccag gttttagagc tagaaatagc                        40

<210> SEQ ID NO 14
<211> LENGTH: 35
<212> TYPE: DNA
<213> ORGANISM: Artificial Sequence
<220> FEATURE:
<223> OTHER INFORMATION: Synthesized

<400> SEQUENCE: 14
aaccttggga tccgcttcag ctgcttcttg gtgcc                             35

<210> SEQ ID NO 15
<211> LENGTH: 36
<212> TYPE: DNA
<213> ORGANISM: Artificial Sequence
<220> FEATURE:
```

<223> OTHER INFORMATION: Synthesized

<400> SEQUENCE: 15
attattggtc tctaaacctt gggatccgct tcagct        36

<210> SEQ ID NO 16
<211> LENGTH: 25
<212> TYPE: DNA
<213> ORGANISM: Artificial Sequence
<220> FEATURE:
<223> OTHER INFORMATION: Synthesized

<400> SEQUENCE: 16
gacaggcgtc ttctactggt gctac        25

<210> SEQ ID NO 17
<211> LENGTH: 25
<212> TYPE: DNA
<213> ORGANISM: Artificial Sequence
<220> FEATURE:
<223> OTHER INFORMATION: Synthesized

<400> SEQUENCE: 17
ctcacaaatt atcagcacgc tagtc        25

<210> SEQ ID NO 18
<211> LENGTH: 25
<212> TYPE: DNA
<213> ORGANISM: Artificial Sequence
<220> FEATURE:
<223> OTHER INFORMATION: Synthesized

<400> SEQUENCE: 18
gactagcgtg ctgataattt gtgag        25

<210> SEQ ID NO 19
<211> LENGTH: 25
<212> TYPE: DNA
<213> ORGANISM: Artificial Sequence
<220> FEATURE:
<223> OTHER INFORMATION: Synthesized

<400> SEQUENCE: 19
ttagtcccac ctcgccagtt tacag        25

<210> SEQ ID NO 20
<211> LENGTH: 25
<212> TYPE: DNA
<213> ORGANISM: Artificial Sequence
<220> FEATURE:
<223> OTHER INFORMATION: Synthesized

<400> SEQUENCE: 20
ttgactagcg tgctgataat ttgtg        25

<210> SEQ ID NO 21
<211> LENGTH: 23
<212> TYPE: DNA
<213> ORGANISM: Artificial Sequence
<220> FEATURE:
<223> OTHER INFORMATION: Synthesized

<400> SEQUENCE: 21
atcaaccgta ctgctgcaaa cag        23

```
<210> SEQ ID NO 22
<211> LENGTH: 23
<212> TYPE: DNA
<213> ORGANISM: Artificial Sequence
<220> FEATURE:
<223> OTHER INFORMATION: Synthesized

<400> SEQUENCE: 22
cgctagcctc cacatgttct cgt                                              23

<210> SEQ ID NO 23
<211> LENGTH: 23
<212> TYPE: DNA
<213> ORGANISM: Artificial Sequence
<220> FEATURE:
<223> OTHER INFORMATION: Synthesized

<400> SEQUENCE: 23
aagaccttga ggatgagcac cag                                              23

<210> SEQ ID NO 24
<211> LENGTH: 21
<212> TYPE: DNA
<213> ORGANISM: Artificial Sequence
<220> FEATURE:
<223> OTHER INFORMATION: Synthesized

<400> SEQUENCE: 24
aagtagcggg agatcccgag t                                                21

<210> SEQ ID NO 25
<211> LENGTH: 30
<212> TYPE: DNA
<213> ORGANISM: Artificial Sequence
<220> FEATURE:
<223> OTHER INFORMATION: Synthesized

<400> SEQUENCE: 25
ctagtctaga atgttttccc attccttcct                                       30

<210> SEQ ID NO 26
<211> LENGTH: 25
<212> TYPE: DNA
<213> ORGANISM: Artificial Sequence
<220> FEATURE:
<223> OTHER INFORMATION: Synthesized

<400> SEQUENCE: 26
cggggtaccg cgtactttct caaag                                            25

<210> SEQ ID NO 27
<211> LENGTH: 19
<212> TYPE: DNA
<213> ORGANISM: Artificial Sequence
<220> FEATURE:
<223> OTHER INFORMATION: Synthesized

<400> SEQUENCE: 27
agctgaagcg gatcccaag                                                   19

<210> SEQ ID NO 28
<211> LENGTH: 20
<212> TYPE: DNA
<213> ORGANISM: Artificial Sequence
<220> FEATURE:
<223> OTHER INFORMATION: Synthesized
```

```
<400> SEQUENCE: 28
agctgaagcg gatctccaag                                                 20

<210> SEQ ID NO 29
<211> LENGTH: 5
<212> TYPE: PRT
<213> ORGANISM: Artificial sequence
<220> FEATURE:
<223> OTHER INFORMATION: Synthesized

<400> SEQUENCE: 29

Arg Arg Arg Arg Arg
1               5

<210> SEQ ID NO 30
<211> LENGTH: 6
<212> TYPE: PRT
<213> ORGANISM: Artificial sequence
<220> FEATURE:
<223> OTHER INFORMATION: Synthesized

<400> SEQUENCE: 30

His His His His His His
1               5

<210> SEQ ID NO 31
<211> LENGTH: 8
<212> TYPE: PRT
<213> ORGANISM: Artificial sequence
<220> FEATURE:
<223> OTHER INFORMATION: Synthesized

<400> SEQUENCE: 31

Asp Tyr Lys Asp Asp Asp Asp Lys
1               5

<210> SEQ ID NO 32
<211> LENGTH: 8
<212> TYPE: PRT
<213> ORGANISM: Artificial sequence
<220> FEATURE:
<223> OTHER INFORMATION: Synthesized

<400> SEQUENCE: 32

Trp Ser His Pro Gln Phe Glu Lys
1               5

<210> SEQ ID NO 33
<211> LENGTH: 10
<212> TYPE: PRT
<213> ORGANISM: Artificial sequence
<220> FEATURE:
<223> OTHER INFORMATION: Synthesized

<400> SEQUENCE: 33

Glu Gln Lys Leu Ile Ser Glu Glu Asp Leu
1               5                   10
```

METHOD FOR IMPROVING SENSITIVITY OF PLANT TO GIBBERELLIN INHIBITOR AND USE THEREOF

INCORPORATION BY REFERENCE

The sequence listing provided in the file entitled Efiled_Sequence_Listing_OA1.txt, which is an ASCII text file that was created on May 6, 2021, and which comprises 25,363 bytes, is hereby incorporated by reference in its entirety.

TECHNICAL FIELD

The present invention relates to a method for increasing the sensitivity of a plant to a gibberellin inhibitor and applications thereof in the field of biotechnology.

BACKGROUND ART

N,N-dimethylpiperidinium chloride (DPC), whose chemical name is 1,1-dimethylpiperidinium chloride, is an inhibitory plant growth regulator that has a retarding effect on plant vegetative growth. It can inhibit cell elongation, reduce the growth of plant apical bud and control its vertical and horizontal growth. After applying DPC to cotton, the leaves are thickened, the leaf color becomes darker, the chlorophyll content increases, and the leaf photosynthetic rate increases (He Zhongpei et al., 1991, Li Piming et al., 1991; Tian Xiaoli et al., 2004). Thus, it is beneficial to the light transmission in the field, and can enhance the light in the lower part of the cotton plant, and inhibit the growth of the main stem of the cotton plant, shorten the internode of the cotton plant and compact the plant type, thereby preventing the cotton plant from vigorous growth and delaying the closure period. DPC can also increase the root activity of cotton plants (Tian Xiaoli et al., 2006), while DPC can also increase the stability of cell membranes and increase the resistance of cotton plants (Shao Lixiang, 2004).

The application of DPC in cotton accounts for more than 80% of the planting area in the whole country. DPC can regulate cotton under the conditions of growing environment in the field. It can inhibit the growth of the main stem of cotton and reduce the plant height by shortening the internode and reducing the number of internodes. It can compact the plant type, effectively control the vigorous growth of cotton and shape the ideal plant type to optimize the economic traits of cotton (He Zhongpei et al., 1991: Reddy et al., 1992). In the process of tomato cultivation, the use of DPC can inhibit the vain growth of tomato plants, increase the content of chlorophyll and soluble sugar in seedlings, reduce the relative conductivity and significantly increase the yield of large fruit tomatoes (Mao Xiujie et al., 1999; Wang Mei et al., 2012). However, the regulating effect of DPC on gramineous crops, such as maize, is not significant and compared with control, the treatment of maize Zhengdan 958 with 1000 mg/L DPC shows no significant difference in plant height and stem diameter (Chen yin, 2012). Some plants are insensitive to DPC, which limits the application of DPC in crop production.

SUMMARY OF THE INVENTION

The technical problem to be solved by the present invention is how to increase the sensitivity of a plant to a gibberellin inhibitor.

In order to solve the above technical problem, the present invention first provides a method for increasing the sensitivity of a plant to a gibberellin inhibitor.

The method for increasing the sensitivity of a plant to a gibberellin inhibitor provided by the present invention, comprising A1) or A2):

A1) increasing the content of a protein in a recipient plant or enhancing the activity of the protein in the recipient plant to obtain a transgenic plant;

A2) introducing the encoding gene of the protein into the recipient plant to obtain a transgenic plant;

the transgenic plant has increased sensitivity to the gibberellin inhibitor compared to the recipient plant;

the protein is named plant height-related protein (HRP) and is a protein of the following a) or b) or c):

a) a protein whose amino acid sequence is set forth in positions 1-821 of SEQ ID NO: 1;

b) a protein whose amino acid sequence is set forth in SEQ ID NO: 1;

c) a fusion protein obtained by attaching tag(s) to the N-terminus or/and C-terminus of a) or b).

Wherein, the amino acid sequence of positions 1-821 of SEQ ID NO: 1 is the amino acid sequence of the plant height-related protein HRP, which is encoded by the plant height-related protein HRP gene with the nucleotide sequence of positions 1-2463 of SEQ ID NO: 2; the amino acid sequence of positions 824-996 of SEQ ID NO: 1 is the amino acid sequence of GFP, which is encoded by the DNA molecule with the nucleotide sequence of positions 2470-2720 of SEQ ID NO: 2.

In order to facilitate the purification of the protein in a), the tags as shown in Table 1 can be attached to the amino terminus or carboxyl terminus of the protein set forth in SEQ ID NO: 1 in the sequence listing.

TABLE 1

Tag sequences

| Tag | Residue | Sequence |
|---|---|---|
| Poly-Arg | 5-6 (usually 5) | RRRRR (SEQ ID NO: 29) |
| Poly-His | 2-10 (usually 6) | HHHHHH (SEQ ID NO: 30) |
| FLAG | 8 | DYKDDDDK (SEQ ID NO: 31) |
| Strep-tag II | 8 | WSHPQFEK (SEQ ID NO: 32) |
| c-myc | 10 | EQKLISEEDL (SEQ ID NO: 33) |

The HRP in the above b) can be artificially synthesized, or can be obtained by synthesizing its encoding gene first and then conducting biological expression. The encoding gene of the HRP in the above b) can be obtained by deleting the codons of one or more amino acid residues, and/or conducting missense mutations of one or more base pairs, and/or attaching the encoding sequences of the tag(s) shown in Table 1 to 5' end and/or 3' end in the DNA sequence set forth in positions 1-2463 of SEQ ID NO: 2 in the sequence listing.

The HRP in the above d) can be artificially synthesized, or can be obtained by synthesizing its encoding gene first and then conducting biological expression. The encoding gene of the HRP in the above d) can be obtained by deleting the codons of one or more amino acid residues, and/or conducting missense mutations of one or more base pairs, and/or attaching the encoding sequences of the tag(s) shown in Table 1 to 5' end and/or 3' end in the DNA sequence set forth in SEQ ID NO: 2 in the sequence listing.

The method further comprises knocking out the CPS gene in the recipient plant. The CPS gene can be a DNA molecule set forth in SEQ ID NO: 4 in the sequence listing. The knockout can specifically be mutating the sequence AGCT-GAAGCGGATCCCAAG of the CPS gene to AGCT-GAAGCGGATCTCCAAG.

In the above methods, the encoding gene of the HRP is a gene shown in following 1) or 2) or 3) or 4) or 5) or 6):
1) a cDNA molecule or DNA molecule with the nucleotide sequence of positions 1-2463 of SEQ ID NO: 2 in the sequence listing;
2) a cDNA molecule or genomic DNA molecule having 75% or more identity to the nucleotide sequence defined by 1) and encoding the HRP;
3) a cDNA molecule or genomic DNA molecule hybridizing to the nucleotide sequence defined by 1) under stringent conditions and encoding the HRP;
4) a cDNA molecule or DNA molecule having the nucleotide sequence of SEQ ID NO: 2 in the sequence listing;
5) a cDNA molecule or genomic DNA molecule having 75% or more identity to the nucleotide sequence defined by 4) and encoding the HRP;
6) a cDNA molecule or genomic DNA molecule hybridizing to the nucleotide sequence defined by 4) under stringent conditions and encoding the HRP.

Wherein, the nucleic acid molecule can be DNA, such as cDNA, genomic DNA or recombinant DNA; the nucleic acid molecule can also be RNA, such as mRNA or hnRNA.

Wherein, the nucleotide sequence of SEQ ID NO: 2 encodes the amino acid sequence set forth in SEQ ID NO: 1.

One of ordinary skill in the art can readily mutate the nucleotide sequence encoding the HRP of the present invention using known methods, such as directed evolution and point mutation methods. Those artificially modified nucleotides having 75% or more identity to the nucleotide sequence of the HRP isolated by the present invention are nucleotide sequences derived from the present invention and equivalent to the sequence of the invention, as long as they encode the HRP and have the function of the HRP.

The term "identity" as used herein refers to sequence similarity to a native nucleotide sequence. The "Identity" includes 75% or more, or 85% or more, or 90% or more, or 95% or more identity to the nucleotide sequence encoding the protein with the amino acid sequence set forth in SEQ ID NO: 1 or positions 1-821 of SEQ ID NO: 1 of the present invention. The identity can be evaluated using the naked eye or computer software. Using computer software, the identity between two or more sequences can be expressed in a percentage (%), which can be used to evaluate the identity between related sequences.

In the above methods, the stringent conditions are: in a solution of 2-SSC, 0.1% SDS, hybridizing at 68° C. and washing the membrane twice, 5 min each time, and then in a solution of 0.5×SSC, 0.1% SDS, hybridizing at 68° C. and washing the membrane twice, 15 min each time; or, in a solution of 0.1×SSPE (or 0.1×SSC), 0.1% SDS, hybridizing at 65° C. and washing the membrane.

The above 75% or more identity can be 80%, 85%, 90% or 95% or more identity.

In one embodiment of the present invention, the encoding gene of the HRP (i.e., the DNA molecule with the nucleotide sequence set forth in positions 1-821 of SEQ ID NO: 2) is introduced into a plant of interest through a HRP gene recombinant expression vector containing an HRP gene expression cassette.

In the above methods, the HRP gene can be first modified as follows and then introduced into the recipient seed plant to achieve a better expression effect:
1) modifying and optimizing the HRP gene according to actual needs to enable efficient expression of the gene; for example, changing the codons of the HRP gene of the present invention to conform to plant preference, according to the preferred codons of the recipient plant, while keeping the amino acid sequence of the HRP gene; during the optimization process, it is preferred to maintain a certain GC content in the optimized encoding sequence to achieve a high level expression of the introduced gene in the plant, wherein the GC content can be 35%, more than 45%, more than 50% or more than about 60%;
2) modifying the gene sequence adjacent to the initiating methionine to enable efficient translation initiation; for example, modifying by using a valid sequence known in plants;
3) linking to various plant-expressed promoters to facilitate its expression in plants; such promoters can include constitutive, inducible, temporal regulation, developmental regulation, chemical regulation, tissue-preferred and tissue-specific promoters; the selection of the promoter will vary with the time and space requirements of the expression, and also depends on the target species; for example, the tissue or organ-specific expression promoter is selected depending on the period of development of the recipient; although it is proven that many promoters derived from the dicotyledons can be functional in monocotyledons, and vice versa, but ideally dicotyledon promoters are selected for expression in dicotyledons, and monocotyledon promoters are selected for expression in monocotyledons;
4) linking to a suitable transcription terminator, which can also increase the expression efficiency of the gene of the present invention; such as, the tm1 derived from CaMV, the E9 derived from rbcS; any available terminator known to function in plants can be linked to the gene of the present invention;
5) introducing an enhancer sequence, such as intron sequence (e.g., derived from Adh1 and bronze1) and viral leader sequence (e.g., derived from TMV, MCMV and AMV).

The HRP gene recombinant expression vector can be introduced into plant cells by conventional biotechnological methods such as Ti plasmid, plant virus vector, direct DNA transformation, microinjection, electroporation (Weissbach, 1998, Method for Plant Molecular Biology VIII, Academy Press, New York, pp. 411-463; Geiserson and Corey, 1998, Plant Molecular Biology (2nd Edition).).

In the above methods, the transgenic plant is understood to include not only the first generation transgenic plant obtained by transforming the HRP gene into the plant of interest, but also its progeny. For the transgenic plant, the gene can be propagated in this species, and the gene can also be transferred to other breeds of the same species, especially to the commercial breeds, by conventional breeding techniques. The transgenic plants include seeds, callus, whole plants and cells.

In order to solve the above technical problem, the present invention further provides the following M1 or M2 product:
M1. the protein;
M2. the biological material related to the protein, which is any one of the following B1) to B20):

B1) a nucleic acid molecule encoding the protein;
B2) an expression cassette containing the nucleic acid molecule of B1);
B3) a recombinant vector containing the nucleic acid molecule of B1),
B4) a recombinant vector containing the expression cassette of B2);
B5) a recombinant microorganism containing the nucleic acid molecule of B1);
B6) a recombinant microorganism containing the expression cassette of B2);
B7) a recombinant microorganism containing the recombinant vector of B3);
B8) a recombinant microorganism containing the recombinant vector of B4);
B9) a transgenic plant cell line containing the nucleic acid molecule of B1);
B10) a transgenic plant cell line containing the expression cassette of B2);
B11) a transgenic plant cell line containing the recombinant vector of B3);
B12) a transgenic plant cell line containing the recombinant vector of B4);
B13) a transgenic plant tissue containing the nucleic acid molecule of B1);
B14) a transgenic plant tissue containing the expression cassette of B2);
B15) a transgenic plant tissue containing the recombinant vector of B3);
B16) a transgenic plant tissue containing the recombinant vector of B4);
B17) a transgenic plant organ containing the nucleic acid molecule of B1);
B18) a transgenic plant organ containing the expression cassette of B2);
B19) a transgenic plant organ containing the recombinant vector of B3);
B20) a transgenic plant organ containing the recombinant vector of B4).

In the above products, the expression cassette containing the nucleic acid molecule encoding the HRP (HRP gene expression cassette) in B2) refers to a DNA capable of expressing the HRP in a host cell, and the DNA can contain not only a promoter that initiates the transcription of the HRP gene, but also a terminator that terminates the transcription of the HRP gene. Further, the expression cassette can further contain an enhancer sequence. The promoters useful in the present invention include, but are not limited to, constitutive promoters, tissue-, organ- and development-specific promoters, and inducible promoters. Examples of the promoters include, but are not limited to, constitutive 35S promoter of Cauliflower mosaic virus: a wound-inducible promoter from tomato, leucine aminopeptidase ("LAP", Chao et al. (1999) Plant Physiol 120: 979-992); chemically-inducible promoter from tobacco, pathogenesis-related 1 (PR1) (induced by salicylic acid and BTH (benzothiadiazole-7-carbothioic acid S-methyl ester); tomato protease inhibitor II promoter (PIN2) or LAP promoter (both of them can be induced by methyl jasmonate); heat shock promoter (U.S. Pat. No. 5,187,267); tetracycline-inducible promoter (U.S. Pat. No. 5,057,422); seed-specific promoters, such as the millet seed-specific promoter pF128 (CN101063139B (Chinese Patent 200710099169.7)), seed storage protein-specific promoters (e.g., promoters of phaseolin, napin, oleosin and soybean beta conglycin (Beachy et al. (1985) EMBO J. 4: 3047-3053)). They can be used alone or in combination with other plant promoters. All references cited herein are incorporated by reference in their entirety. Suitable transcription terminators include, but are not limited to, *Agrobacterium* nopaline synthase terminator (NOS terminator), Cauliflower mosaic virus CaMV 35S terminator, tm1 terminator, pea rbcS E9 terminator and nopaline and octopine synthase terminator (see, for example, Odell et al. ($1^{985}$) Nature 313: 810; Rosenberg et al. (1987) Gene, 56: 125; Guerineau et al. (1991) Mol. Gen. Genet, 262: 141; Proudfoot (1991) Cell, 64: 671; Sanfacon et al. Genes Dev., 5: 141; Mogen et al. (1990) Plant Cell, 2: 1261; Munroe et al. (1990) Gene, 91:151; Ballad et al. (1989) Nucleic Acids Res. 17:7891; Joshi et al. (1987) Nucleic Acid Res., 15:9627).

The recombinant vector containing the HRP gene expression cassette can be constructed using an existing expression vector. The plant expression vector includes a binary *Agrobacterium* vector and a vector which can be used for plant microprojectile bombardment and the like, such as pAHC25, pBin438, pCAMBIA1302, pCAMBIA2301, pCAMBIA1301, pCAMBIA1300, pBI121, pCAMBIA1391-Xa or pCAMBIA1391-Xb (CAMBIA). The plant expression vector can further contain the 3'-untranslated region of a foreign gene, i.e., containing a polyadenylation signal and any other DNA fragment involved in mRNA processing or gene expression. The polyadenylation signal can direct polyadenosinic acid to the 3' end of the mRNA precursor, for example the 3'-untranslated region of the transcription of the *Agrobacterium* crown gall tumor-inducing (Ti) plasmid genes (such as nopaline synthase gene Nos) and plant genes (such as soybean storage protein gene) both have similar functions. When constructing a plant expression vector using the gene of the present invention, an enhancer, including a translation enhancer or a transcription enhancer, can be used, and these enhancer regions can be an ATG initiation codon or a contiguous region initiation codon, etc., but are required to be identical to the reading frames of the encoding sequence in order to ensure correct translation of the entire sequence. The sources of the translation control signals and initiation codons are broad and can be natural or synthetic. The translation initiation region can be from a transcription initiation region or a structural gene. In order to facilitate the identification and screening of transgenic plant cells or plants, the plant expression vector used can be processed, such as introducing a gene which can be expressed in plants and encode an enzyme that can produce color changes or luminous compound (GUS gene, luciferase gene and the like), marker genes of antibiotics (such as the nptII gene conferring resistance to kanamycin and related antibiotics, the bar gene conferring resistance to the herbicide phosphinothricin, the hph gene conferring antibiotic resistance to hygromycin, the dhfr gene conferring resistance to methotrexate and the EPSPS gene conferring resistance to glyphosate) or chemical-resistant marker gene (such as anti-herbicide gene), and mannose-6-phosphate isomerase gene that provides the ability to metabolize mannose. From the safety of transgenic plants, the transformed plants can be directly screened by adversity without introducing any selectable marker genes.

In the above products, the vector can be a plasmid, a cosmid, a phage or a viral vector.

In the above products, the microorganism can be yeast, bacteria, algae or fungi, such as *Agrobacterium*.

In the above products, none of the transgenic plant cell line, the transgenic plant tissue and the transgenic plant organ includes the propagation material.

In one embodiment of the present invention, the encoding gene of the HRP (i.e., the DNA molecule set forth in positions 1-2463 of SEQ ID NO: 2) is introduced into *Agrobacterium tumefaciens* GV3101 by a recombinant vector containing an expression cassette containing the encoding gene of the HRP. The recombinant vector is the recombinant vector pSuper1300-HRP obtained by replacing the DNA fragment between the Xba I and Kpn I recognition sequences of the vector pSuper1300 with the DNA molecule set forth in positions 1-2463 of SEQ ID NO: 2. The only difference between the pSuper1300-HRP and the pSuper1300 is that the DNA fragment between the Xba I and Kpn I recognition sequences of the pSuper1300-HRP is replaced with the DNA molecule set forth in positions 1-2463 of SEQ ID NO: 2. The recombinant vector pSuper1300-HRP expresses the protein set forth in SEQ ID NO: 1.

In the above products, the nucleic acid molecule of B1) can be the gene shown in the above 1) or 2) or 3) or 4) or 5) or 6).

In order to solve the above technical problem, the present invention further provides any one of the following N1-N4 uses:

N1. use of the method for regulating plant height;
N2. use of the product for regulating plant height;
N3. use of the product for cultivating a plant having increased sensitivity to a gibberellin inhibitor;
N4. use of the product for cultivating a plant having an increased plant height.

In the above uses, the plant is a transgenic plant.

In the above uses, the use of N4 comprises the step of introducing the encoding gene of the HRP into a recipient plant to obtain a transgenic plant; the transgenic plant has an increased plant height compared to the recipient plant.

In the above uses, the use of N1 or N2 comprises S1) and S2):
S1) introducing the encoding gene of the HRP into the recipient plant to obtain a transgenic plant;
S2) administering a gibberellin inhibitor to the transgenic plant to obtain a plant having a reduced plant height compared to the transgenic plant.

In the above uses, the encoding gene of the HRP is the DNA molecule of SEQ ID NO: 2 in the sequence listing.

In one embodiment of the present invention, the encoding gene of the HRP (i.e., the DNA molecule set forth in positions 1-821 of SEQ ID NO: 2) is introduced into a plant of interest through a HRP gene recombinant expression vector containing an HRP gene expression cassette.

In the above uses, the HRP gene can be first modified as follows and then introduced into the recipient seed plant to achieve a better expression effect:
1) modifying and optimizing the HRP gene according to actual needs to enable efficient expression of the gene; for example, changing the codons of the HRP gene of the present invention to conform to plant preference, according to the preferred codons of the recipient plant, while keeping the amino acid sequence of the HRP gene; during the optimization process, it is preferred to maintain a certain GC content in the optimized encoding sequence to achieve a high level expression of the introduced gene in the plant, wherein the GC content can be 35%, more than 45%, more than 50% or more than about 60%;
2) modifying the gene sequence adjacent to the initiating methionine to enable efficient translation initiation; for example, modifying by using a valid sequence known in plants;
3) linking to various plant-expressed promoters to facilitate its expression in plants; such promoters can include constitutive, inducible, temporal regulation, developmental regulation, chemical regulation, tissue-preferred and tissue-specific promoters; the selection of the promoter will vary with the time and space requirements of the expression, and also depends on the target species; for example, the tissue or organ-specific expression promoter is selected depending on the period of development of the recipient; although it is proven that many promoters derived from the dicotyledons can be functional in monocotyledons, and vice versa, but ideally dicotyledon promoters are selected for expression in dicotyledons, and monocotyledon promoters are selected for expression in monocotyledons;
4) linking to a suitable transcription terminator, which can also increase the expression efficiency of the gene of the present invention; such as, the tm1 derived from CaMV, the E9 derived from rbcS; any available terminator known to function in plants can be linked to the gene of the present invention;
5) introducing an enhancer sequence, such as intron sequence (e.g., derived from Adh1 and bronze1) and viral leader sequence (e.g., derived from TMV, MCMV, and AMV).

The HRP gene recombinant expression vector can be introduced into plant cells by conventional biotechnological methods such as Ti plasmid, plant virus vector, direct DNA transformation, microinjection, electroporation (Weissbach, 1998, Method for Plant Molecular Biology VIII, Academy Press, New York, pp. 411-463; Geiserson and Corey, 1998, Plant Molecular Biology (2nd Edition).).

In the above uses, the transgenic plant is understood to include not only the first generation transgenic plant obtained by transforming the HRP gene into the plant of interest, but also its progeny. For the transgenic plant, the gene can be propagated in this species, and the gene can also be transferred to other breeds of the same species, especially to the commercial breeds, by conventional breeding techniques. The transgenic plants include seeds, callus, whole plants and cells.

In the present invention, the gibberellin inhibitor can be a gibberellin synthesis inhibitor such as a gibberellin biosynthesis inhibitor. The gibberellin inhibitor can specifically be DPC. The DPC can specifically be a product of Jiangsu Runze Agrochemical Co., Ltd., and the catalog number is HG/T2856-1997.

In the present invention, the plant can be a dicotyledon or a monocotyledon. The dicotyledon can be a cruciferous plant, such as *Arabidopsis thaliana*. The monocotyledon can specifically be maize.

In the present invention, the increase in sensitivity to the gibberellin inhibitor is manifested in that the plant height reduction rate of the transgenic plant is higher than that of the recipient plant under the same increase in the concentration of the gibberellin inhibitor. For example, the plant height reduction rate of the 30 mg/L DPC-treated transgenic plant with the HRP gene was 33.92% relative to the plant height of the 0 mg/L DPC-treated transgenic plant with the HRP gene, and the plant height reduction rate of the 30 mg/L DPC-treated recipient plant was 13.60% relative to the plant height of the 0 mg/L DPC-treated recipient plant.

DETAILED DESCRIPTION OF THE INVENTION

Figure 1:
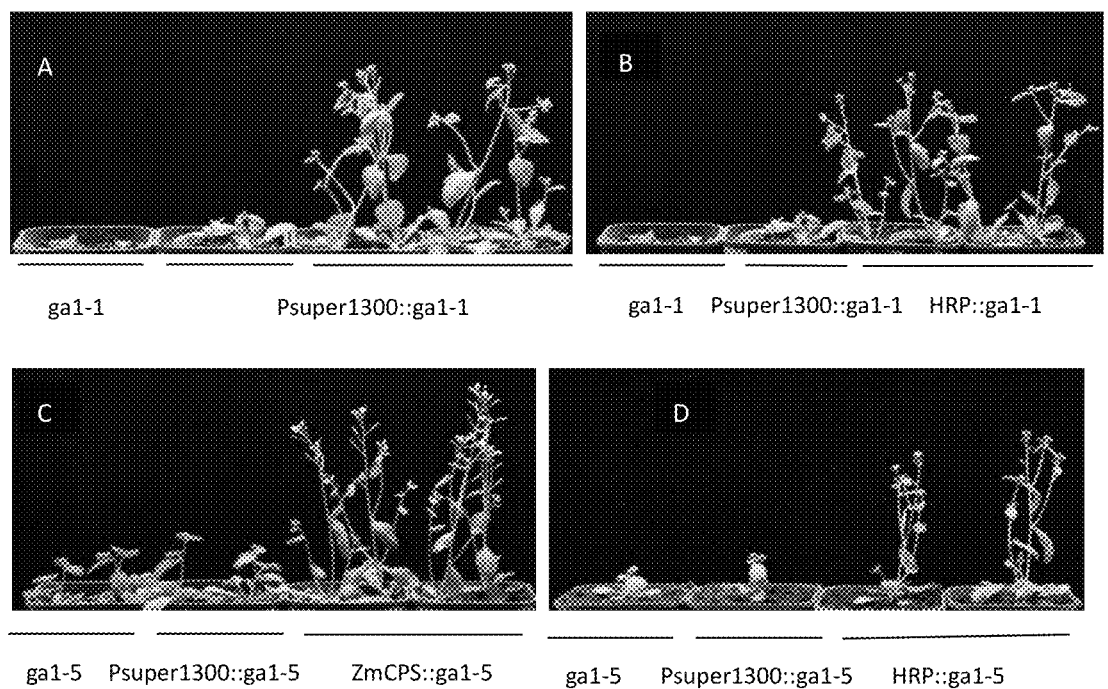
FIG. 1 shows the plant heights of transgenic *Arabidopsis thaliana* with the HRP gene and the ZmCPS gene before DPC treatment. Wherein, A shows the plant height of ZmCPS::ga1-1, B shows the plant height of HRP::ga1-1, C shows the plant height of ZmCPS::ga1-5, and D shows the plant height of HRP::ga1-5.

The present invention is further described in detail below with reference to the specific embodiments. The examples are given only to illustrate the present invention and are not intended to limit the scope of the present invention.

The experimental methods in the following examples are conventional methods unless otherwise specified.

The materials, reagents and the like used in the following examples are commercially available unless otherwise specified.

The vector pSuper1300 in the following examples is the pSuper1300::GFP in the literature (*Lipid transfer protein 3 as a target of MYB96 mediates freezing and drought stress in Arabidopsis*, Journal of Experimental Botany, Guo et al., Vol. 64, No. 6, pp. 1755-1767, 2013). This biological material is available to the public from the applicant, and is only used for repeating the related experiments of the present invention and cannot be used for other purposes.

The *Agrobacterium tumefaciens* GV3101 in the following examples is the *Agrobacterium* strain GV3101 in the literature (A Plasma Membrane Receptor Kinase, GHR1, Mediates Abscisic Acid- and Hydrogen Peroxide-Regulated Stomatal Movement in *Arabidopsis*, Hua et al., The Plant Cell, Vol. 24: 2546-2561, June 2012). This biological material is available to the public from the applicant, and is only used for repeating the related experiments of the present invention and cannot be used for other purposes.

The *Arabidopsis thaliana* mutants ga1-1 and ga1-5 in the following examples are products of the Ohio State University *Arabidopsis thaliana* Biological Resource Center.

The 0 mg/L DPC solution in the following examples is ultrapure water, and the 30 mg/L DPC solution in the following examples is a solution obtained by adding 30 mg of DPC to 1 L of ultrapure water, 500 mg/L DPC solution in the following examples is a solution obtained by adding 500 mg of DPC to 1 L of ultrapure water.

In the following examples, the growth conditions of *Arabidopsis thaliana* are: culturing in a growth chamber with a photoperiod of 16 h light/8 h dark, a light intensity of 60 μmol/m$^2$/s, a humidity of 60%-70%, and a temperature of 22° C.

The DPC in the following examples is a product of Jiangsu Runze Agrochemical Co., Ltd., the catalog number is HG/T2856-1997, and the DPC is a gibberellin biosynthesis inhibitor.

Example 1. Regulation of *Arabidopsis thaliana* Plant Height Using a Set of Reagents Regulating Plant Height The set of reagents regulating plant height consists of a plant height-related protein and N,N-dimethylpiperidinium chloride (DPC, also known as 1,1-dimethylpiperidinium chloride); the plant height-related protein is named HRP, whose amino acid sequence is positions 1-821 of SEQ ID NO: 1 in the sequence listing. The gene of the plant height-related protein (HRP) is the DNA molecule set forth in positions 1-2463 of SEQ ID NO: 2.

The HRP gene is derived from *G. arboreum* Shixiyal (SXYI) (Li et al., Genome sequence of the cultivated cotton *Gossypium arboreum*, Nature GenNetics VOLUME 46 NUMBER 6 Jun. 2014). The gene of the plant height-related protein HRP is the DNA molecule set forth in SEQ ID NO: 2 in the sequence listing.

1. Construction of Recombinant Vector and Recombinant *Agrobacterium*

The fragment between the Xba I and Kpn I recognition sequences of the vector pSuper1300 was replaced with the DNA molecule set forth in positions 1-2463 of SEQ ID NO:2 (i.e., the HRP gene) to obtain the recombinant vector pSuper1300-HRP. The only difference between the pSuper1300-HRP and the pSuper1300 is that the DNA fragment between the Xba I and Kpn I recognition sequences of the pSuper1300-HRP is replaced with the DNA molecule set forth in positions 1-2463 of SEQ ID NO:2. The recombinant vector pSuper1300-HRP expresses a fusion protein formed by the plant height-related protein HRP and GFP and set forth in SEQ ID NO: 1.

Wherein, the amino acid sequence of positions 1-821 of SEQ ID NO: 1 is the amino acid sequence of the plant height-related protein HRP, which is encoded by the plant height-related protein HRP gene set forth in positions 1-2463 of SEQ ID NO: 2; the amino acid sequence of positions 824-996 of SEQ ID NO: 1 is the amino acid sequence of GFP, which is encoded by the DNA molecule set forth in positions 2470-2720 of SEQ ID NO: 2.

The fragment between the Spe I and Kpn I recognition sequences of the vector pSuper1300 was replaced with the DNA molecule set forth in positions 1-2565 of SEQ ID NO: 3 to obtain the recombinant vector pSuper1300-ZmCPS. The only difference between the pSuper1300-ZmCPS and the pSuper1300 is that the DNA fragment between the Spe I and Kpn I recognition sequences of the pSuper1300-ZmCPS was replaced with the DNA molecule set forth in SEQ ID NO: 3. The recombinant vector pSuper1300-ZmCPS expresses a fusion protein formed by the protein encoded by positions 1-2565 of SEQ ID NO: 3 and GFP.

Wherein, positions of 1-2565 of SEQ ID NO: 3 is the nucleotide sequence of the ZmCPS gene, and the ZmCPS gene is derived from maize (B73).

The pSuper1300-HRP was introduced into the *Agrobacterium tumefaciens* GV3101 to obtain a recombinant strain, and the recombinant strain was named GV3101-pSuper1300-HRP; the pSuper1300-ZmCPS was introduced into the *Agrobacterium tumefaciens* GV3101 to obtain a recombinant strain, and the recombinant strain was named GV3101-pSuper1300-ZmCPS: the pSuper1300 was introduced into the *Agrobacterium tumefaciens* GV3101 to obtain a recombinant strain, and the recombinant strain was named GV3101-pSuper1300.

2. Construction of Transgenic *Arabidopsis thaliana*

The transgenic *Arabidopsis thaliana* was constructed by transforming the *Arabidopsis thaliana* mutants ga1-1 and ga1-5 with the GV3101-pSuper1300-HRP, GV3101-pSuper1300-ZmCPS and GV3101-pSuper1300 of step 1, respectively. The method of transforming the *Arabidopsis thaliana* mutant ga1-1 with the HRP gene was as follows:

2.1 Cultivation of *Arabidopsis thaliana*: the mutant ga1-1 seeds were vernalized at 4° C. for 72 h, seeded in gibberellin medium (the gibberellin medium was a solid medium having a $GA_3$ concentration of $10^{-4}$ M, which was obtained by adding gibberellin (GA3) to MS medium), moved in a growth chamber at 22° C., 16 h light/8 h dark, light intensity of 60 μmol/m²/s and humidity of 60%-70%. When cultured and grown to 4 pieces of euphylla, the mutants were transplanted into planting pots having mixed nutrient soil and vermiculite with equal proportion, wherein the mutants should be sprayed with $10^{-4}$ M $GA_3$ every two days.

2.2 Preparation of *Agrobacterium* liquid: the *Agrobacterium* inoculated with the GV3101-pSuper1300-HRP, which was detected to be correct and subjected to streak-culture, was inoculated into 5 ml of YEP liquid medium (containing antibiotics), and cultured at 28° C., 220 rpm for 30 h. The obtained liquid was transferred to 50 ml of YEP (containing antibiotics) with a volume ratio of 1:100, cultured at 28° C., 220 rpm overnight, until an OD600 of 0.6-0.8 was reached; the resulting culture was centrifuged at 6000 g for 15 min at 4° C., and the bacteria were collected and resuspended in ½ MS+5% sucrose solution, 0.02%-0.05% Silwet L-77 (a surfactant product from AMRESCO, USA) was added before the transformation.

2.3 Transformation: after the *Arabidopsis thaliana* plant was flowering, the top of the main branch was cut off to promote the development of the lateral branches. Within 6 days after pruning, the inflorescence without revealing white of the *Arabidopsis thaliana* was wetted using the prepared *Agrobacterium*. The transformed *Arabidopsis thaliana* was wrapped in a black plastic bag filled with air, and the black plastic bag was removed after 24 hours of dark. The light was restored and the plants were grown to firmness in the normal manner, and the mature $T_1$ generation seeds of the transgenic ga1-1 with the HRP gene (HRP::ga1-1) were harvested.

Homozygous line plants of the HRP::ga1-1 were obtained as follows: ① the $T_1$ generation HRP::ga1-1 seeds were seeded on MS solid medium containing hygromycin for screening, and the hygromycin-resistant positive plants with healthy and dark green euphylla and roots extending into the medium were transferred to soil, and $T_2$ generation HRP::ga1-1 seeds were harvested; ② the $T_2$ generation HRP::ga1-1 seeds were seeded on MS solid medium containing hygromycin to obtain $T_2$ generation HRP::ga1-1 plants, and the plants were screened using hygromycin, and the $T_2$ generation HRP::ga1-1 plants, in which the ratio of the hygromycin-resistant plants to the hygromycin-sensitive plants was 3:1, were selected and the hygromycin-resistant plants were transplanted into soil, and $T_3$ generation HRP::ga1-1 seeds were harvested (the hygromycin-resistant plants showed that the euphylla were dark green and the roots were extending into the medium; the hygromycin-sensitive plants showed that the euphylla were yellow and the roots were not extending); ③ the $T_3$ generation HRP::ga1-1 seeds were seeded on MS medium containing hygromycin to obtain $T_3$ generation HRP::ga1-1 plants, and the plants were screened using hygromycin, the $T_3$ generation HRP::ga1-1 plants, all of which were resistant to hygromycin, were selected and transplanted into soil to obtain the homozygous line plants of the HRP::ga1-1.

According to the above method, the ga1-1 was replaced with the ga1-5, and the other steps were unchanged, and the transgenic ga1-1 with the HRP gene which was named HRP::ga1-1 and its homozygous line plants were respectively obtained.

According to the above method, the GV3101-pSuper1300-HRP was replaced with the GV3101-pSuper1300-ZmCPS and GV3101-pSuper1300, respectively, and the other steps were unchanged and the transgenic ga1-1 with the ZmCPS gene which was named ZmCPS::ga1-1 and its homozygous line plants and the transgenic ga1-1 with the empty vector which was named pSuper1300::ga1-1 and its homozygous line plants were obtained, respectively.

According to the above method, the ga1-1 was replaced with the ga1-5, the GV3101-pSuper1300-HRP was replaced with the GV3101-pSuper1300-ZmCPS and GV3101-pSuper1300 and the other steps were unchanged, and the transgenic ga1-5 with the ZmCPS gene which was named ZmCPS::ga1-5 and its homozygous line plants and the transgenic ga1-5 with the empty vector which was named pSuper1300::ga1-5 and its homozygous line plants were obtained, respectively.

3. Identification of Transgenic Plants 3.1 Detection of HRP Gene Expression in Homozygous Line Transgenic *Arabidopsis Thaliana* with the HRP Gene The expression level of the HRP gene in the homozygous line plant of the HRP::ga1-1 and the homozygous line plant of the HRP::ga1-5 in step 2 and the expression level of the ZmCPS gene in the homozygous line plant of the ZmCPS::ga1-1 and the homozygous line plant of the ZmCPS::ga1-5 in step 2 were identified by Real-Time PCR. The primers for detecting the expression level of the HRP gene were 5'-ACCGAGGACTCGCAGAGTTA-3' (SEQ ID NO: 5) and 5'-ACCTTTAGCATTTGGCGATG-3' (SEQ ID NO: 6), and the primers for detecting the expression level of the ZmCPS gene were 5'-TGCAGCCACTTATCGACCAG-3' (SEQ ID NO: 7) and 5'-AGGCGAGGGTGTTGATCATG-3' (SEQ ID NO: 8). The internal reference was the AtUbI gene, and the primers of the internal reference were 5'-ATTACCC-GATGGGCAAGTCA-3' (SEQ ID NO: 9) and 5'-CACAAACGAGGGCTGGAACA-3' (SEQ ID NO: 10). The results showed that the HRP gene expressed in both homozygous line plant of the HRP::ga1-1 and the homozygous line plant of the HRP::ga1-5, and the ZmCPS gene expressed in both the homozygous line plant of the ZmCPS::ga1-1 and homozygous line plant of the ZmCPS::ga1-5.

3.2 Detection of the HRP in the Homozygous Line Transgenic *Arabidopsis thaliana* with the HRP Gene Western blot was used to identify the HRP protein in the homozygous line plant of the HRP::ga1-1 and the homozygous line plant of the HRP::ga1-5 of step 2, and the ZmCPS protein in the pure line plant of the ZmCPS::ga1-1 and the homozygous line plant of the ZmCPS::ga1-5 and the primary antibody was Anti-GFP Tag Rabbit (a product from Roche, catalog number: 14717400). The results showed that the HRP protein expressed in both the homozygous line plant of the HRP::ga1-1 and the homozygous line plant of the HRP::ga1-5, the ZmCPS protein expressed in both the homozygous line plant of the ZmCPS::ga1-1 and the homozygous line plant of the ZmCPS::ga1-5.

4. Effect of DPC on the Plant Height of the Transgenic *Arabidopsis thaliana* with the HRP Gene The experiment was repeated three times, and the specific steps of each repeated experiment were as follows:

4.1 DPC Could Reduce the Plant Height of the Transgenic *Arabidopsis thaliana* with the HRP Gene Thirty homozygous line plants of the HRP::ga1-1 of step 2 were randomly selected and randomly divided into three According to the above method, the ga1-1 was replaced with the ga1-5, the other steps were unchanged, and untreated ga1-5, 30 mg/L DPC-treated ga1-5, and 500 mg/L DPC-treated ga1-5 were obtained, respectively.

Figure 2:
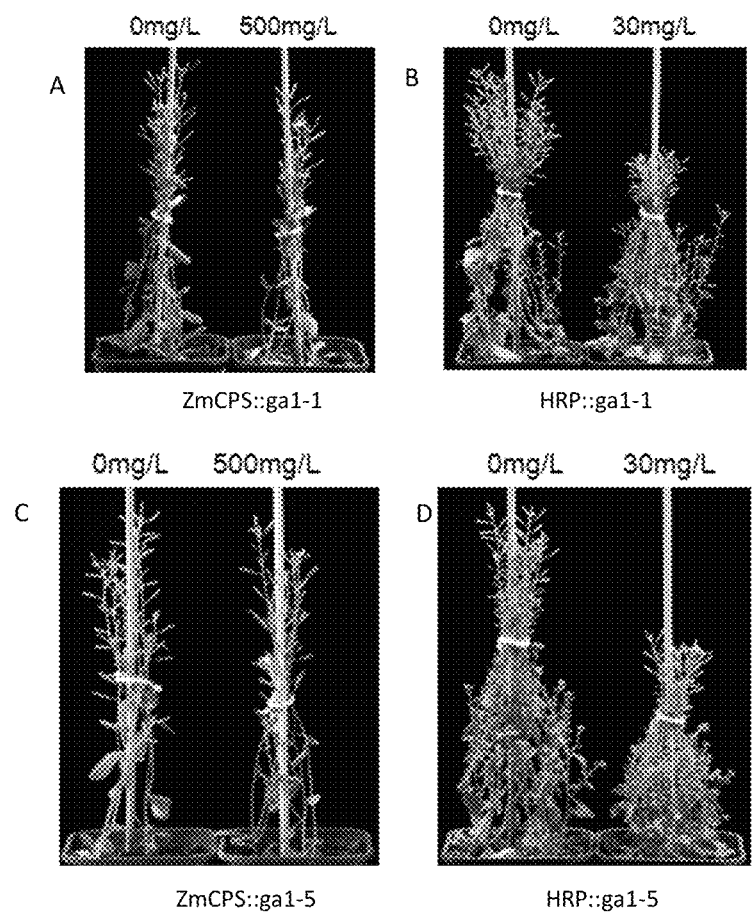
FIG. 2 shows the plant heights of differently treated *Arabidopsis thaliana*. Wherein, A shows the plant heights of ZmCPS::ga1-1 treated with different concentrations of DPC, B shows the plant heights of HRP::ga1-1 treated with different concentrations of DPC, C shows the plant heights of ZmCPS::ga1-5 treated with different concentrations of DPC, and D shows the plant heights of HRP::ga1-5 treated with different concentrations of DPC.

The plant heights of the above *Arabidopsis thaliana* before the treatment (FIG. 1) and after different treatments (FIG. 2 and Table 2) were measured.

TABLE 2

Plant height and plant height reduction rate of differently treated *Arabidopsis thaliana*

| | DPC concentration (mg/L) | | | | |
| --- | --- | --- | --- | --- | --- |
| | 0 | 30 | | 500 | |
| Plant | Plant height (cm) | Plant height (cm) | Plant height reduction rate | Plant height (cm) | Plant height reduction rate |
| HRP::ga1-1 | 16.95 ± 0.21 | 11.2 ± 0.24 | 33.92% | 6.75 ± 0.38 | 60.18% |
| ZmCPS::ga1-1 | 16.5 ± 0.23 | 16.52 ± 0.31 | −0.12% | 16.45 ± 0.21 | 0.30% |
| pSuper1300::ga1-1 | 4.55 ± 0.25 | 4.33 ± 0.27 | 4.84% | 3.98 ± 0.17 | 12.53% |
| ga1-1 | 4.78 ± 0.30 | 4.13 ± 0.25 | 13.60% | 3.95 ± 0.10 | 17.36% |
| HRP::ga1-5 | 15.88 ± 0.29 | 10.80 ± 0.43 | 31.99% | 6.41 ± 0.18 | 59.63% |
| ZmCPS::ga1-5 | 16.8 ± 0.24 | 16.79 ± 0.13 | 0.06% | 16.66 ± 0.31 | 0.83% |
| pSuper1300::ga1-5 | 6.95 ± 0.44 | 6.54 ± 0.20 | 5.90% | 6.21 ± 0.14 | 10.65% |
| ga1-5 | 7.03 ± 0.68 | 6.55 ± 0.10 | 6.83% | 6.40 ± 0.12 | 8.96% | groups, ten plants in each group. On the 33rd day of sowing (the day of sowing was recorded as the first day of sowing), the plants of these three groups were treated as follows, respectively one group was sprayed with water (i.e., 0 mg/L DPC solution) and cultured for 12 days to obtain untreated HRP::ga1-1; one group was sprayed with 30 mg/L DPC solution and cultured for 12 days to obtain 30 mg/L DPC-treated HRP::ga1-1; the last group was sprayed with 500 mg/L aqueous DPC solution and cultured for 12 days to obtain 500 mg/L DPC-treated HRP::ga1-1.

According to the above method, the homozygous line plants of the HRP::ga1-1 were replaced with the homozygous line plants of the HRP::ga1-5, the homozygous line plants of the ZmCPS::ga1-1, the homozygous line plants of the ZmCPS::ga1-5, the homozygous line plants of the PsSuper1300::ga1-1 and the homozygous line plants of the PsSuper1300::ga1-5 respectively, the other steps were unchanged, and untreated HRP::ga1-5, 30 mg/L DPC-treated HRP::ga1-5, 500 mg/L DPC-treated HRP::ga1-5, untreated ZmCPS::ga1-1, 30 mg/L DPC-treated ZmCPS::ga1-1, 500 mg/L DPC-treated ZmCPS::ga1-1, untreated ZmCPS::ga1-5, 30 mg/L DPC-treated ZmCPS::ga1-5, 500 mg/L DPC-treated ZmCPS::ga1-5, untreated PsSuper1300::ga1-1, 30 mg/L DPC-treated PsSuper1300::ga1-1, 500 mg/L DPC-treated PsSuper1300::ga1-1, untreated PsSuper1300::ga1-5, 30 mg/L DPC-treated PsSuper1300::ga1-5 and 500 mg/L DPC-treated PsSuper1300::ga1-5 were obtained, respectively.

When the ga1-1 was cultured to the 33rd day of sowing (the day of sowing was recorded as the first day of sowing), 30 plants were taken and randomly divided into three groups, ten plants in each group and the plants of these three groups were treated as follows, respectively: one group was sprayed with 0 mg/L DPC solution and cultured for 12 days to obtain untreated ga1-1; one group was sprayed with 30 mg/L aqueous DPC solution and cultured for 12 days to obtain 30 mg/L DPC-treated ga1-1; the last group was sprayed with 500 mg/L DPC solution and cultured for 12 days to obtain 500 mg/L DPC-treated ga1-1.

The results showed that under the same DPC concentration, the difference in plant height reduction rate between the pSuper1300::ga1-1 and the ga1-1 after DPC treatment was not significant, and basically DPC had no effect on ZmCPS::ga1-1, and the plant height reduction rate of the DPC-treated HRP::ga1-1 was much higher than the pSuper1300::ga1-1 and ga1-1 treated with the corresponding DPC concentration; the plant height reduction rate of the 30 mg/L DPC-treated HRP::ga1-1 was 2.49 times that of the ga1-1; the plant height reduction rate of the 500 mg/L DPC-treated HRP::ga1-1 was 3.47 times that of the ga1-1. Under the same DPC concentration, the difference in plant height reduction rate between the pSuper1300::ga1-5 and the ga1-5 after DPC treatment was not significant, and basically DPC had no effect on ZmCPS::ga1-5, and the plant height reduction rate of the DPC-treated HRP::ga1-5 was much higher than the pSuper1300::ga1-5 and ga1-5 treated with the corresponding DPC concentration; the plant height reduction rate of the 30 mg/L DPC-treated HRP::ga1-5 was 4.68 times that of ga1-5; the plant height reduction rate of the 500 mg/L DPC-treated HRP::ga1-5 was 6.66 times that of ga1-5. It was indicated that the HRP could increase the sensitivity of *Arabidopsis thaliana* to DPC.

The results showed that the plant height-related protein HRP of the present invention could increase the plant height of *Arabidopsis thaliana*: the plant heights of the untreated HRP::ga1-1, 30 mg/L DPC-treated HRP::ga1-1 and 500 mg/L DPC-treated HRP::ga1-1 were 1.03 times, 0.68 times and 0.41 times that of the correspondingly treated ZmCPS::ga1-1, respectively, and 3.54 times, 2.71 times and 1.71 times that of the correspondingly treated ga1-1, respectively; the plant heights of the untreated HRP::ga1-5, 30 mg/L DPC-treated HRP::ga1-5 and 500 mg/L DPC-treated HRP::ga1-5 were 0.95 times, 0.64 times and 0.38 times that of the correspondingly treated ZmCPS::ga1-5, respectively, and 2.26 times, 1.65 times and 1.00 times that of the correspondingly treated ga1-5, respectively.

4.2 Effects of Different Concentrations of DPC on Plant Height of the Transgenic *Arabidopsis thaliana* with the HRP Gene Seventy homozygous line plants of the HRP::ga1-1 of step 2 were randomly selected and randomly divided into seven groups, ten plants in each group. On the 33rd day of sowing (the day of sowing was recorded as the first day of sowing), the plants of these seven groups were treated as follows, respectively: one group was sprayed with water (i.e., 0 mg/L aqueous DPC solution) and cultured for 12 days to obtain untreated HRP::ga1-1; one group was sprayed with 30 mg/L aqueous DPC solution and cultured for 12 days to obtain 30 mg/L DPC-treated HRP::ga1-1; one group was sprayed with 50 mg/L aqueous DPC solution and cultured for 12 days to obtain 50 mg/L DPC-treated HRP::ga1-1; one group was sprayed with 100 mg/L aqueous DPC solution and cultured for 12 days to obtain 100 mg/L DPC-treated HRP::ga1-1; one group was sprayed with 300 mg/L aqueous DPC solution and cultured for 12 days to obtain 300 mg/L DPC-treated HRP::ga1-1; one group was sprayed with 500 mg/L aqueous DPC solution and cultured for 12 days to obtain 500 mg/L DPC-treated HRP::ga1-1; one group was sprayed with 1000 mg/L aqueous DPC solution and cultured for 12 days to obtain 1000 mg/L DPC-treated HRP::ga1-1.

According to the above method, the homozygous line plant of the HRP::ga1-1 was replaced with the pure homozygous line plant of the HRP::ga1-5, and the other steps were unchanged to obtain untreated HRP::ga1-5, 30 mg/L DPC-treated HRP::ga1-5, 50 mg/L DPC-treated HRP::ga1-5, 100 mg/L DPC-treated HRP::ga1-5, 300 mg/L DPC-treated HRP::ga1-5, 500 mg/L DPC-treated HRP::ga1-5 and 1000 mg/L DPC-treated HRP::ga1-5, respectively.

Figure 3:
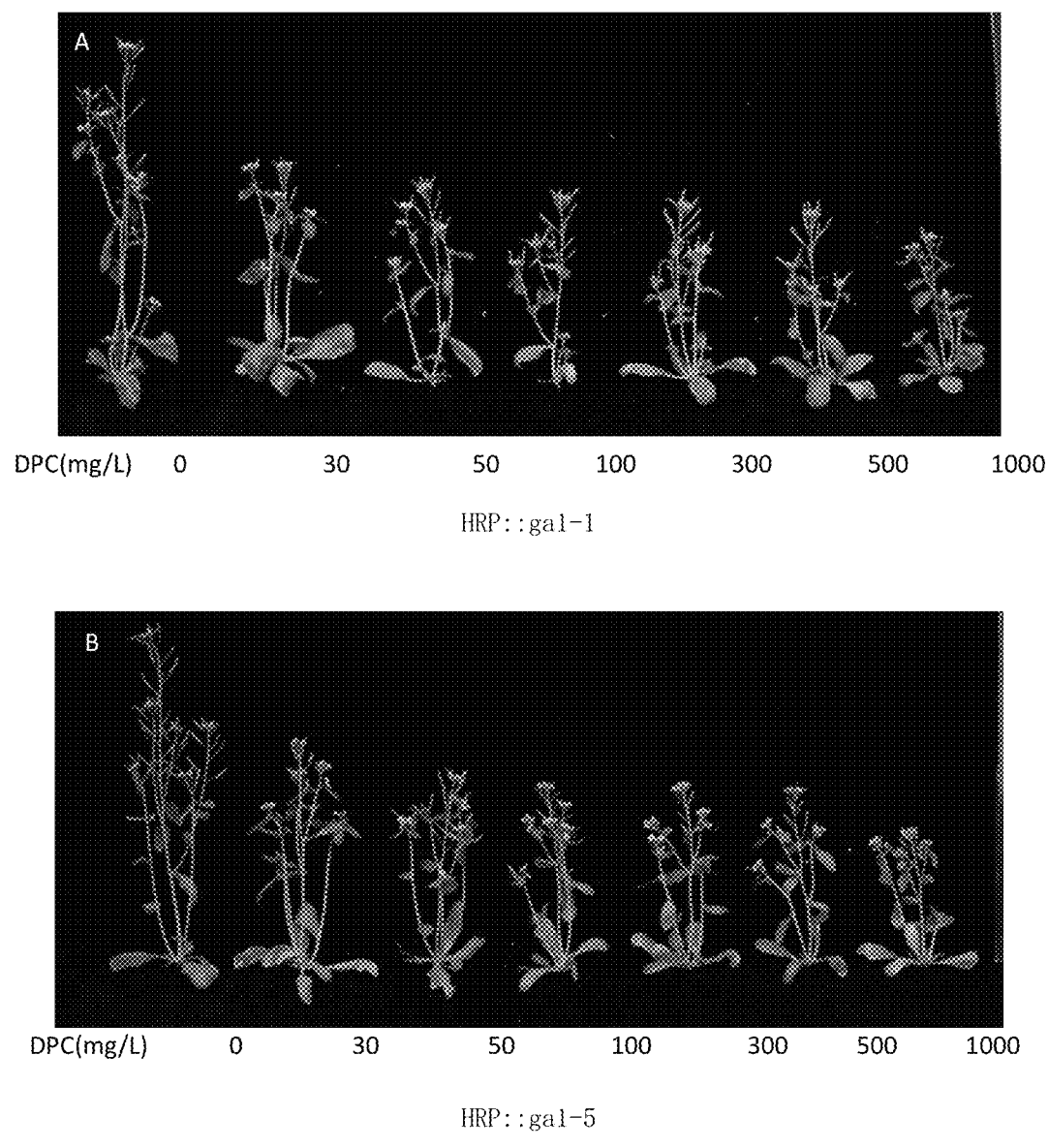
FIG. 3 shows the plant heights of HRP::ga1-1 and HRP::ga1-5 treated with different concentrations of DPC. Wherein, A shows the plant heights of HRP::ga1-1 treated with different concentrations of DPC; B shows the plant heights of HRP::ga1-5 treated with different concentrations of DPC.

The plant heights of the differently treated *Arabidopsis thaliana* were measured respectively (FIG. 3), and the average plant heights are shown in Table 3.

The results showed that the plant height of the transgenic *Arabidopsis thaliana* with the HRP gene was affected by the concentration of DPC, and the plant height of the transgenic *Arabidopsis thaliana* with the HRP gene decreased with the increase of DPC concentration.

ing, the zmcps Knock out mutant (ZmCPSKO, Zmcps-ko) plants were successfully obtained.

Please refer to the method of Professor Chen Qijun of China Agricultural University (Xing H L, Dong L, Wang Z P, et al. A CRISPR/Cas9 toolkit for multiplex genome editing in plants [J]. BMC Plant Biology, 2014, 14(1): 327.) for the CRISPR protocol—the construction of the pBUE411-2gR vector, PCR identification and sequencing confirmation.

ZmCPS Gene Sequence:

(SEQ ID NO: 4)
ATGAAGCTCCTCTCGCCGGCGGCCGCACCGTCGTCCTCGCCGTT

GTTCCCTCCTCGCATCGTCGAAGCTGCAGCTCGTCAATCAGGTC

CATGCCGTATCCGCATCCGTATCCGTGGCAAAGCAGCAGCAGCA

GGAGGAGGAGGAGGCGCGGGCGCGACGGGGCCCCGCGGCAGCCT

CAGGCTCGCCGGGTGGTGGAGAGCGCAGCAGCAGGCCCCGGCCA

CGGCGACGACAACGCAGCAGCCTGACAACGTCTCCAGTGCTAAA

GTGTTCCAGACCAGCCGTGTGGAAACCGAGTCCGAAATTGCGAA

ATGGCCAGGGAAACCACAAGTAGCGGGAGATCCCGAGTGCTGAG

GAGGCAGAGCTGCAGCCACTTATCGACCAGGTGAGGGCGATGCT

ACGGTCGATGAACGACGGGATACCAGCGCCTCGGCGTACGACA

CGGCGTGGGTGGCGATGGTGCCGAAGGTGGGCGGCGACGGCGGC

GCCCAGCCCCAGTTCCCGGCCACCGTGCGCTGGATCGTGGACC

ACCAGCTGCCCGACGGCTCCTGGGGCGACTCGGCCCTGTTCTCC

GCCTACGACCGCATGATCAACACCCTCGCCTGCGTCGTCGCGCT

GACCAAGTGGTCGCTGGAGCCCGCGAGGTGCGAGGCGGGGCTCT

CGTTCCTGCACGAGAACATGTGGAGGCTAGCGGAGGAGGAGGCG

GAGTCGATGCCCATCGGCTTCGAGATCGCCTTCCCTTCTCTCAT

TABLE 3

Plant height (cm) of the transgenic *Arabidopsis thaliana* with the HRP gene treated with different concentrations of DPC

| Plant | DPC concentration (mg/L) | | | | | | |
|---|---|---|---|---|---|---|---|
| | 0 | 30 | 50 | 100 | 300 | 500 | 1000 |
| HRP::ga1-1 | 16.07143 | 9.714286 | 9.314286 | 9.342857 | 8.857143 | 8.585714 | 7.242857 |
| HRP::ga1-5 | 15.98571 | 11.92857 | 9.842857 | 10.14286 | 9.957143 | 9.857143 | 7.357143 |

Example 2: Sensitivity Analysis of the Transgenic Zmcps-Ko Plants with the HRP to DPC I. Dwarf Zmcps Ko Mutant Plants were Obtained Using CRISPR Technology.

The pBUE411-2gR CRISPR-Cas9 ZmCPS vector was successfully constructed, and the vector was successfully transformed into the maize embryos using the method of infecting the immature embryos of the maize inbred line B73 (Schnable P S, Wilson R K. The B73 maize genome: complexity, diversity, and dynamics. [J]. Science, 2009, 326 (5956): 1112.) (WT) with the *Agrobacterium*, the ZmCPS was knocked out and the target sequence used was AGCT-GAAGCGGATCCCAAG (SEQ ID NO: 11). After screen- -continued

CCAGACGGCTAGGGACCTGGGCGTCGTCGACTTCCCGTACGGAC

ACCCGGCGCTGCAGAGCATATACGCCAACAGGGAAGTCAAGCT

GAAGCGGATCCCAAGGGACATGATGCACAGGGTCCCGAC

GTCCATCCTGCACAGCCTTGAAGGGATGCCTGACCTGGACT

GGCCGAGGCTTCTGAACCTCCAGTCCTGCGACGGCTCCTTCTT

GTTCTCTCCTTCGGCTACCGCTTACGCGCTGATGCAAACCGGT

GACAAGAAGTGCTTCGAATACATCGACAGGATTGTCAAAAAA

TTCAACGGGGAGTCCCCAATGTTTATCCGGTCGATCTTTT

```
CGAGCACATCTGGGTTGTGGATCGGTTGGAGCGACTCGGGATCT

CCCGCTACTTCCAACGAGAGATTGAGCAGTGCATGGACTATGT

GAACAGGCACTGGACTGAAGATGGGATTTGCTGGGCTAGGAAAT

CCAATGTGAAGGATGTGGATGACACAGCTATGGCTTTCCGACTACT

AAGGCTACATGGATACAATGTCTCTCCAAGTGTGTTTAAGAACTTT

GAGAAAGATGGAGAGTTCTTTTGTTTTGTGGGCCAATCGACTCA

AGCCGTCACTGGGATGTATAACCTCAACAGAGCCTCTCAGATAAG

TTTTCAAGGAGAGGATGTATTGCAGTGCTAGGGTTTTCTCGTATG

AGTTTCTGAGACAGAGAGAAGAACAAGGCATGATCCGTGATAAAT

GGATCGTTGCCAAGGATCTACCTGGCGAGGTGCAATATACACTAG

ACTTCCCTTGGTATGCAAGCTTGCCTCGTGTAGAGGCAAGAACCTA

TCTAGATCAATATGGTGGTAAAGATGACGTTTGGATTGGAAAGACA

CTCTACAGGATGCCTCTTGTGAATAACGACACATATCTAGAGTTGG

CAATAAGGGATTTCAACCATTGCCAAGCTCTGCATCAGCTTGAG

TGTAATGGGCTGCAAACGTGGTACAAGGATAATTGCCTTGACGCT

TTTGGAGTAGAACCACAAGATGTTTTAAGATCTTACTTTTTAGCT

GCTGCTTGCATTTTTGAACCTAGCCGTGCTGCTGAGCGGCTTGCAT

GGGCTAGAACGTCAATGATTGCCAATGCCATTTCTACACATCTTCG

TGACATTTCGGAAGACAAGAAGAGATTGGAATGTTTCGTGCACTG

TCTCTATGAAGAAAACGATGTATCATGGCTTAAACGAAATCCTAA

TGATGTTATTCTTGAGAGGGCACTTCGAAGATTAATTAACTTATTA

GCACAAGAAGCATTGCCAATTCATGAAGGACAAAGATTCATACACA

GTCTATTGAGTCTTGCATGGACCGAATGGATGTTGCAAAAGGCA

AATAAAGAAGAAAACAAATATCACAAATGCAGTGGTATAGAACC

ACAATACATGGTTCATGATAGGCAAACATACTTACTTTTAGTTCAG

GTTATTGAGATTTGTGCTGGACGAATTGGTGAGGCTGTGTCAATGA

TAAACAACAAGGATAATGATTGGTTTATTCAACTCACATGTGCT

ACTTGTGACAGTCTTAACCATAGGATGTTACTGTCCCAGGATACTA

TGAAGAATGAAGCAAGAATAAATTGGATTGAGAAGGAAATCGAGTT

GAATATGCAAGAGCTTGCTCAATCTCTCCTTTTGAGATGTGATGAG

AAAACTAGCAATAAGAAGACCAAGAAAACCTTATGGGATGTCCTAA

GAAGTTTATACTATGCTACTCATTCCCCACAACATATGATCGAT

AGACATGTTTCCAGAGTTATCTTTGAGCCTGTTTAA
```

The Primers were as Follows:

```
MT1-BsF:
                                       (SEQ ID NO: 12)
ATATATGGTCTCTGGCGAAATTGCGAAATGGCCAGGTT

MT1-F0:
                                       (SEQ ID NO: 13)
TGAAATTGCGAAATGGCCAGGTTTTAGAGCTAGAAATAGC

MT2-R0:
                                       (SEQ ID NO: 14)
AACCTTGGGATCCGCTTCAGCTGCTTCTTGGTGCC

MT2-BsR:
                                       (SEQ ID NO: 15)
ATTATTGGTCTCTAAACCTTGGGATCCGCTTCAGCT
```

The underlined were the recognition sequences of Msc1 and BamH1.

PCR amplification: the 100-fold dilution of pCBC-MT1T2 (Xing H L, Dong L, Wang Z P et al. A CRISPR/Cas9 toolkit for multiplex genome editing in plants [J]. BMC Plant Biology, 2014, 14(1): 327.) was used as the template for a four primer PCR amplification. −BsF/−BsR concentration was within the normal primer range, −F0/−R0 was diluted 20 times.

The PCR product was purified and recovered and the following restriction-ligation system was established:

| Component | Volume | Reaction conditions |
|---|---|---|
| 1. PCR fragment (964-bp) | 2 | 5 hours at 37° C. |
| 2. pBUE411 | 2 | 5 min at 50° C. |
| 3. 10xNEB T4 Buffer | 1.5 | 10 min at 80° C. |
| 4. 10xBSA | 1.5 | |
| 5. BsaI (NEB) | 1 | |
| 6. T4 Ligase (NEB)/high concentration | 1 | |
| 7. ddH2O | 6 | |
| 8. Total | 15 | |

5 μl of the PCR product was taken to transform the E. coli competent cells. Kan plate was used for screening. OsU3-FD3+TaU3-RD=831 bp, colony PCR identification was performed, and OsU3-FD3 and TaU3-FD2 were confirmed by sequencing.

Note 1: Colony PCR and Sequencing Primers:

```
OsU3-FD3:
                                       (SEQ ID NO: 16)
GACAGGCGTCTTCTACTGGTGCTAC

TaU3-RD:
                                       (SEQ ID NO: 17)
CTCACAAATTATCAGCACGCTAGTC
                                       (SEQ ID NO: 18)
[rc: GACTAGCGTGCTGATAATTTGTGAG]

TaU3-FD:
                                       (SEQ ID NO: 19)
TTAGTCCCACCTCGCCAGTTTACAG

TaU3-FD2:
                                       (SEQ ID NO: 20)
TTGACTAGCGTGCTGATAATTTGTG
```

The steps of Agrobacterium-mediated transformation of maize immature embryos were as follows:
1. Materials and Methods
1.1 Experimental Materials
1.1.1 Plant Material
Maize (Zea mays L.) inbred line B73 (Schnable P S, Wilson R K. The B73 maize genome: complexity, diversity, and dynamics. [J]. Science, 2009, 326 (5956): 1112.)
1.1.2 Experimental Strain
Agrobacterium EHA105 (with high infection rate to monocotyledons)
1.1.3 Plasmid Vector
The CRISPR/Cas9 system-related plasmids were provided by Professor Chen Qijun: pBUE411; pCBC-MT1T1T2.

1.2 Configuration of Common Media and Solutions
1.2.1 Configuration of Common Media LB medium: 10 g of tryptone, 10 g of NaCl, 5 g of yeast extract. In case of a solid medium, 15 g of agar was further added. The final volume was made up to 1 L.

YEP medium: 10 g of tryptone, 5 g of NaCl, 10 g of yeast extract. In case of a solid medium, 15 g of agar was further added. The final volume was made up to 1 L.

YEB medium: 10 g of tryptone, 5 g of sucrose, 1 g of yeast extract, 0.5 g of $MgSO_4 \cdot 7H_2O$. In case of a solid medium, 15 g of agar was further added. The final volume was made up to 1 L.

1.2.2 Configuration of Mother Liquors (1) N6 macro-elements (mother liquor concentration 20×): 2 L

| Component | Final concentration (mg/L) | Mass (g) |
| --- | --- | --- |
| $CaCl_2 \cdot 2H_2O$ | 166 | 6.64 |
| $KNO_3$ | 2830 | 113.2 |
| $(NH_4)_2SO_4$ | 463 | 18.52 |
| $KH_2PO_4$ | 400 | 16.00 |
| $MgSO_4 \cdot 7H_2O$ | 185 | 7.40 |

Preparation method of 2 L mother liquor: 6.64 g of $CaCl_2 \cdot 2H_2O$ was weighed and dissolved in 700 mL of distilled water, and then the remaining four components were weighed and dissolved in 700 mL of distilled water. After the two solutions were completely dissolved, they were mixed and the final volume was made up to 2 L.

(2) B5 micro-elements (mother liquor concentration 100×): 1 L

| Component | Final concentration (mg/L) | Mass (g) |
| --- | --- | --- |
| $MnSO_4 \cdot H_2O$ | 10.00 | 2.00 |
| $ZnSO_4 \cdot 7H_2O$ | 2.00 | 0.40 |
| $CoCl_2 \cdot 6H_2O$ | 0.025 | 0.005 |
| $CuSO_4 \cdot 5H_2O$ | 0.025 | 0.005 |
| $NaMoO_4 \cdot 2H_2O$ | 0.25 | 0.05 |
| KI | 0.75 | 0.15 |
| $H_3BO_3$ | 3.00 | 0.60 |

(3) Fe salt (mother liquor concentration 100×) 1 L

| Component | Final concentration (mg/L) | Mass (g) |
| --- | --- | --- |
| $FeSO_4 \cdot 7H_2O$ | 27.80 | 2.78 |
| $Na_2EDTA$ | 37.30 | 3.73 |

Method: $Na_2EDTA$ was dissolved in hot water and then $FeSO_4 \cdot 7H_2O$ was gradually dissolved in the $Na_2EDTA$ solution and the final volume was made up to 1 L.

(4) RT V (mother liquor concentration 200×): 1 L

| Component | Final concentration (mg/L) | Mass (g) |
| --- | --- | --- |
| Choline chloride | 0.0977 | 0.0195 |
| Riboflavin | 0.0489 | 0.0098 |
| Biotin | 0.1002 | 0.02 |
| Folic acid | 0.0485 | 0.0097 |
| Niacin | 0.1994 | 0.0399 |
| Vitamin B1 | 0.4722 | 0.0944 |
| D-calcium pantothenate | 0.10 | 0.02 |
| Pyridoxine Hydrochloride | 0.1994 | 0.0399 |
| Vitamin B12 | 0.0001 | 0.00675 g dissolved in 100 mL water (+400 μL) |
| Para-aminobenzoic acid | 0.0494 | 0.0099 |

The above various vitamins were dissolved in water, and the folic acid was first dissolved in 1 mL of dilute ammonia water, and then distilled water was added to a final volume of 1 L.

(5) MS macro-elements (mother liquor concentration 20×): 1 L

| Component | Mass (g) |
| --- | --- |
| $CaCl_2 \cdot 2H_2O$ | 8.80 |
| $NH_4NO_3$ | 33 |
| $KNO_3$ | 38 |
| $MgSO_4 \cdot 7H_2O$ | 7.4 |
| $KH_2PO_4$ | 3.4 |

(6) MS micro-elements (mother liquor concentration 200×): 500 mL

| Component | Mass (g) |
| --- | --- |
| KI | 0.083 |
| $H_3BO_3$ | 0.62 |
| $MnSO_4 \cdot H_2O$ | 2.23 |
| $ZnSO_4 \cdot 7H_2O$ | 0.86 |
| $NaMoO_4 \cdot 2H_2O$ | 0.025 |
| $CuSO_4 \cdot 5H_2O$ | 0.0025 |
| $CoCl_2 \cdot 6H_2O$ | 0.0025 |

(7) MS organic matter (mother liquor concentration 200×): 500 mL

| Component | Mass (g) |
| --- | --- |
| Myo-inositol | 10 |
| Niacin | 0.05 |
| Pyridoxine hydrochloride | 0.05 |
| Thiamin hydrochloride | 0.01 |
| Glycine | 0.2 |

(8) Fe salt (mother liquor concentration 100×): 1 L

| Component | Mass (g) |
| --- | --- |
| $FeSO_4 \cdot 7H_2O$ | 2.78 |
| $Na_2EDTA$ | 3.73 |

Method: $Na_2EDTA$ was dissolved in hot water and then $FeSO_4 \cdot 7H_2O$ was gradually dissolved in the $Na_2EDTA$ solution and water was added to a final volume of 1 L.

1.2.3 Configuration of the Media Used to Transform the Maize

| Amount (Calculated in 1 L) | Basic | Infection | Co-culture | Recover | Screening | Induciton | Differentiation | Rootage |
|---|---|---|---|---|---|---|---|---|
| N6 macro-elements (20×) | 50 mL | 50 mL | 50 mL | 50 mL | 50 mL | 50 mL | 50 mL | — |
| B5 micro-elements (200×) | 5 mL | 5 mL | 5 mL | 5 mL | 5 mL | 5 mL | 5 mL | — |
| MS macro-elements (20×) | — | — | — | — | — | — | — | 25 mL |
| MS micro-elements (200×) | — | — | — | — | — | — | — | 2.5 mL |
| MS organic matter (200×) | — | — | — | — | — | — | — | 2.5 mL |
| Fe salt (100×) | 10 mL | 10 mL | 10 mL | 10 mL | 10 mL | 10 mL | 10 mL | 10 mL |
| RTV organic matter (200×) | 5 mL | 5 mL | 5 mL | 5 mL | 5 mL | 5 mL | 5 mL | — |
| Glycine | 40 mg | 40 mg | 40 mg | 40 mg | 40 mg | 40 mg | 40 mg | — |
| Casein hydrolysate | 0.2 g | 0.2 g | 0.2 g | 0.2 g | 0.2 g | 0.2 g | 0.2 g | — |
| L-proline | 0.7 g | 0.7 g | 0.7 g | 0.7 g | 0.7 g | 0.7 g | 0.7 g | — |
| Myo-inositol | 0.1 g | 0.1 g | 0.1 g | 0.1 g | 0.1 g | 0.1 g | 0.1 g | — |
| Sucrose | 30 g | 68.5 g | 30 g | 30 g | 30 g | 50 g | 30 g | 15 g |
| Glucose | — | 36 g | — | — | — | — | — | — |
| Hygromycin (5 mg/L) | — | — | — | — | 100 μL | 100 μL | 100 μL | — |
| Glufosinate (10 mg/L) | — | — | — | — | 5-10 mg | 5 mg | 5 mg | — |
| 2,4-D (1 mg/mL) | 2.0 mg | 2.0 mg | 2.0 mg | 2.0 mg | 2.0 mg | — | — | — |
| NAA(1 mg/mL) | — | — | — | — | — | — | — | 0.2 mg |
| Cef (100 mg/mL) | — | — | — | 2.5 mL | 2.5 mL | 2.5 mL | — | — |
| AS (200 mmoL/L) | — | 500 μL | 500 μL | — | — | — | — | — |
| AgNO$_3$(5 mg/mL) | — | 170 μL | 170 μL | 170 μL | — | — | — | — |
| DTT(0.15 mg/mL) | — | 1 mL | 1 mL | — | — | — | — | — |
| Cys(300 mg/mL) | — | 1 mL | 1 mL | — | — | — | — | — |
| pH | 5.8 | 5.2 | 5.8 | 5.8 | 5.8 | 5.8 | 5.8 | 5.8 |
| Plant gel | — | 3 g | 3 g | 3 g | 3 g | 3 g | 3 g | 3 g |
| Agar powder | 7.5 g | — | — | — | — | — | — | — |

1.2.4 Configuration of the Common Solutions

Amp (100 mg/mL): 5 g of Amp was weighed and dissolved in sterile water and the final volume was made up to 50 mL. The solution was filtered, sterilized, subpackaged and stored at −20° C.

Kan (100 mg/mL): 5 g of Kan was weighed and dissolved in sterile water and the final volume was made up to 50 mL. The solution was filtered, sterilized, subpackaged and stored at −20° C.

Rif (50 mg/mL): 0.5 g of Rif was weighed and dissolved in DMSO and the final volume was made up to 10 mL. The solution was filtered, sterilized, subpackaged and stored at −20° C.

AS (200 mmoL/L): 0.3924 g of AS drug was weighed and dissolved in DMSO and the final volume was made up to 10 mL. The solution was filtered, sterilized, subpackaged and stored at −20° C. without light.

Cef (100 mg/mL): 25 g of Cef was weighed and dissolved in sterile water and the final volume was made up to 250 mL. The solution was filtered, sterilized, subpackaged and stored at −20° C.

Cb (100 mg/mL): 25 g of Cb was weighed and dissolved in sterile water and the final volume was made up to 250 mL. The solution was filtered, sterilized, subpackaged and stored at −20° C.

AgNO$_3$ (5 mg/mL): 50 mg of AgNO$_3$ was weighed and dissolved in sterile water and the final volume was made up to 10 mL. The solution was filtered, sterilized, subpackaged and stored at −20° C. without light. Note: Wear gloves when configuring.

Glufosinate (10 mg/L): 100 mg of glufosinate was weighed and dissolved in 10 ml of sterile water, filtered, sterilized, subpackaged and stored at −20° C.

6-BA (2 mg/mL): 0.2 g of 6-BA was weighed and dissolved in 1 mol/L NaOH. After 6-BA was completely dissolved, water was added to a final volume of 100 mL. The solution was filtered, sterilized, subpackaged and stored at 4° C.

2,4-D (1 mg/mL): 100 mg of 2,4-D was weighed and dissolved in a small amount of absolute ethanol, and sterile water was added to a final volume of 100 mL. The solution was filtered, sterilized, subpackaged and stored at 4° C.

NAA (1 mg/mL): 100 mg of NAA was weighed and dissolved in a small amount of 1 mol/L NaOH. After NAA was completely dissolved, sterile water was added to a final volume of 100 mL. The solution was filtered, sterilized, subpackaged and stored at 4° C.

1.3 Transformation of Maize Immature Embryos with *Agrobacterium*

1.3.1 Pollination of Maize (1) When the female ear appeared, it was bagged in time. After the filament drew out, the female ear was pollinated. The bag was kept until the harvest;

(2) After the pollination, a small card recording the male parent and the female parent or pollination method and pollination date was hung. The maize was harvested after 10-12 days.

1.3.2 Peeling of Immature Embryos (1) B73 female ear with an immature embryo of 1.5-2.0 mm was taken at 10-12 days after pollination;

(2) The bract, filament and the head and tail of the female ear were removed from the newly harvested female ear; a gun-type tweezer was inserted from the top into the female ear; after the maize was sprayed with alcohol, it was taken to the clean bench and soaked in a wild-mouth bottle containing 70% alcohol for 3 minutes;

(3) The female ear was taken out and placed in an empty petri dish for later use;

(4) The tweezer was hold in the left hand and the upper part of the grain was cut using a scalpel equipped with a No. 22 blade in the right hand;

(5) Using a No. 10 blade, the tip of the blade was inserted between the peel and the endosperm of the lower part of the grain, the endosperm was picked out, the immature embryo was gently peeled, and placed in a 2 mL centrifuge tube containing the infecting solution (containing AS and AgNO$_3$);

Precautions in the Process of Peeling the Embryo:
(1) The infecting solution is configured in advance, AS is added before use (500 μL of AS is added to 1 L of infecting solution, AS is added before use, the infecting solution is dispensed into vials before use to avoid cross-contamination; the infecting solution should not be placed for too long, and if precipitation occurs, the solution needs to be reconfigured;
(2) The infecting solution with AS added needs to be dispensed into 2 mL centrifuge tubes, and the sterilized centrifuge tubes are prepared in advance; generally, one centrifuge tube was for one plant of maize; the centrifuge tubes should be protected from light and covered with newspaper; AS must be added before use because its activation takes time;
(3) When peeling the embryo, pollution should be avoided; generally, after the embryo is peeled, it is washed with the infecting solution at least twice, 30 seconds each time.

1.3.3 Preparation of Agrobacterium Liquid

The preserved Agrobacterium liquid was taken out from the −80° C. refrigerator in advance, and after sufficient thawing, 200 μl of the Agrobacterium liquid was added to 30 mL of LB medium (containing Kan, Rif), and cultured at 26° C. and 180 rpm overnight. On the next day, when the culture became cloudy, it was taken out from the shaker and the secondary activation was conducted. 3-5 mL of the culture was added to 30 mL of LB medium, cultured on a shaker (180 rpm) at 26° C. for 4-6 hours. Be sure to add AS to the liquid (3 μl AS per 30 mL liquid) one hour before use. The culture prepared by the shake cultivation was separately poured into two 50 mL centrifuge tubes and centrifuged, and the centrifuge was set at 26° C., 4000 rpm, 10 min. After centrifugation, the supernatant was discarded, and then the bacteria were resuspended by adding the infecting solution and the OD value was adjusted to 0.6-0.8. Note that when adding the infecting solution, add a small amount first, if not enough, add more infecting solution and if the OD value is high, add more infecting solution to adjust it for later use.

1.3.4 Agrobacterium Infection of Immature Embryos
(1) The infecting solution in the centrifuge tube for storing the immature embryos was sucked out and 1.5 ml of the prepared Agrobacterium liquid was added; the centrifuge tube stood vertically for 15 minutes;
(2) A sterilized empty dish was prepared, 2-3 layers of filter paper were spread inside, and then a layer of filter paper was spread in the maize co-culture medium;
(3) After 15 minutes, the immature embryos were poured together with the Agrobacterium liquid in a petri dish with sterile filter papers, and dried in a clean bench, but the immature embryos were not dehydrated;
(4) The blow-dried immature embryos were transferred to the co-culture medium with the scutellum facing up, and co-cultured for three days in the dark at 24° C.;

1.3.5 Recovery, Screening, Differentiation and Rooting of Maize Transformation Materials
(1) Recovery culture: the immature embryos co-cultured for three days were transferred to the recovery medium (if the co-cultured immature embryos are polluted with bacteria, carefully pick the immature embryos polluted with bacteria into 2 ml sterilized centrifuge tubes or flasks and wash the bacteria with sterile water until the water is clear, then wash with sterile water containing 100 mg/mL cephalosporin for 30 min, and finally pour the immature embryos into the culture dish with sterile filter papers, then transfer the immature embryos to the recovery medium) and cultured in the dark at 28° C. for 7 days;
(2) Screening culture: the immature embryos obtained in the recovery culture were transferred to the screening medium for dark culture, subcultured every two weeks; the number of screening and screening concentration depends on the situation (in this method, the conditions were: PPT screening, twice to 3 times, screening pressure was 5-10 mg/L);
(3) Inducing differentiation culture: the screened callus was transferred to the induction medium (high sugar medium), and cultured in the dark for two weeks;
(4) Differentiation culture: the resistant callus obtained after two weeks of recovery culture was transferred to the differentiation medium, subjected to light culture (light cycle was light/dark: 16 h/8 h), and subcultured every two weeks;
(5) Rooting culture: when the differentiated seedlings grew to have more than 1 to 2 leaves, the seedlings were cut from the resistant callus and transferred to a wild-mouth bottle for rooting culture; when the regeneration seedlings grew to the mouth of the bottle and enough lateral roots grew on the roots, hardening-seedling could be performed;
(6) Hardening-seedling and transplantation of the regeneration seedlings: after the seedlings were moved to the greenhouse for 2-3 days, the sealing film was opened, a layer of sterile water was added, and then the seedlings were cultured for 2-3 days; then the seedlings were transplanted into small pots and before transplanting, the medium on the roots of the seedlings was rinsed with tap water; after the seedlings were relatively strong, they were moved into the big pots in the greenhouse for further culture.

1.4 Detection of Positive Plant

After the seedlings grew to 4 leaf expansion phase, the young leaves were taken for detection and identification.

PCR amplification and sequencing were performed to identify the target fragment.

The primers for PCR and sequencing detection for the mutant transgenic material:

```
Target1F
                                  (SEQ ID NO: 21)
ATCAACCGTACTGCTGCAAACAG Target1R
                                  (SEQ ID NO: 22)
CGCTAGCCTCCACATGTTCTCGT Target2F
                                  (SEQ ID NO: 23)
AAGACCTTGAGGATGAGCACCAG Target2R
                                  (SEQ ID NO: 24)
AAGTAGCGGGAGATCCCGAGT
```

The primers for the detection of the target fragment of the transgenic plant:

```
Cotton HRP-CDS-F
                                  (SEQ ID NO: 25)
CTAGTCTAGAATGTTTTCCCATTCCTTCCT Cotton HRP-CDS-R
                                  (SEQ ID NO: 26)
CGGGGTACCGCGTACTTTCTCAAAG
```

Figure 4:
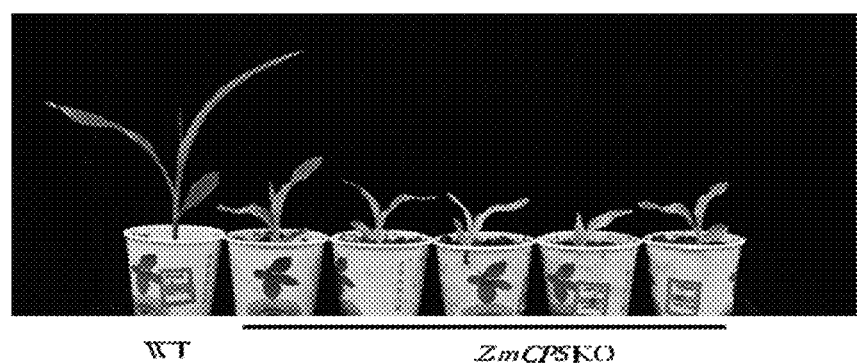
FIG. 4 shows the plant phenotypes of ZmCPSKO and WT.

Compared with WT, the plant sequenced to have a mutated sequence had an inserted base, resulting in the entire protein being misinterpreted. The target sequence AGCTGAAGCGGATCCCAAG (SEQ ID NO: 27) was mutated to AGCTGAAGCGGATCTCCAAG (SEQ ID NO: 28). The other sequences of the ZmCPS gene could not encode, and finally the active CPS protein could not be synthesized, resulting in the gibberellin could not be synthesized in the downstream of the GA synthesis pathway which in turn caused dwarfing of the plant (FIG. 4).

2. Sensitivity Analysis of the Transgenic Zmcps-Ko Line with HRP to DPC

The GV3101-pSuper1300-HRP of Example 1 was transformed into the ZmCPSKO maize embryos of step 1.1 by using the *Agrobacterium* to infect the maize immature embryos, and positive transgenic maize with the HRP was obtained by screening, and the transgenic maize with the HRP contained the target gene HRP. The GV3101-pSuper1300-ZmCPS and GV3101-pSuper1300 were used as controls, and the ZmCPS control maize and empty vector control maize were obtained, respectively.

The WT and transgenic plants were sprayed with DPC during jointing stage to test their DPC sensitivity: the whole plant was sprayed with 500 ppm (5 mM) DPC when the maize was grown to 7 leaf expansion phase and 12 leaf expansion phase. Plant height and ear height were measured 2 weeks after treatment and after tasseling.

Figure 5:
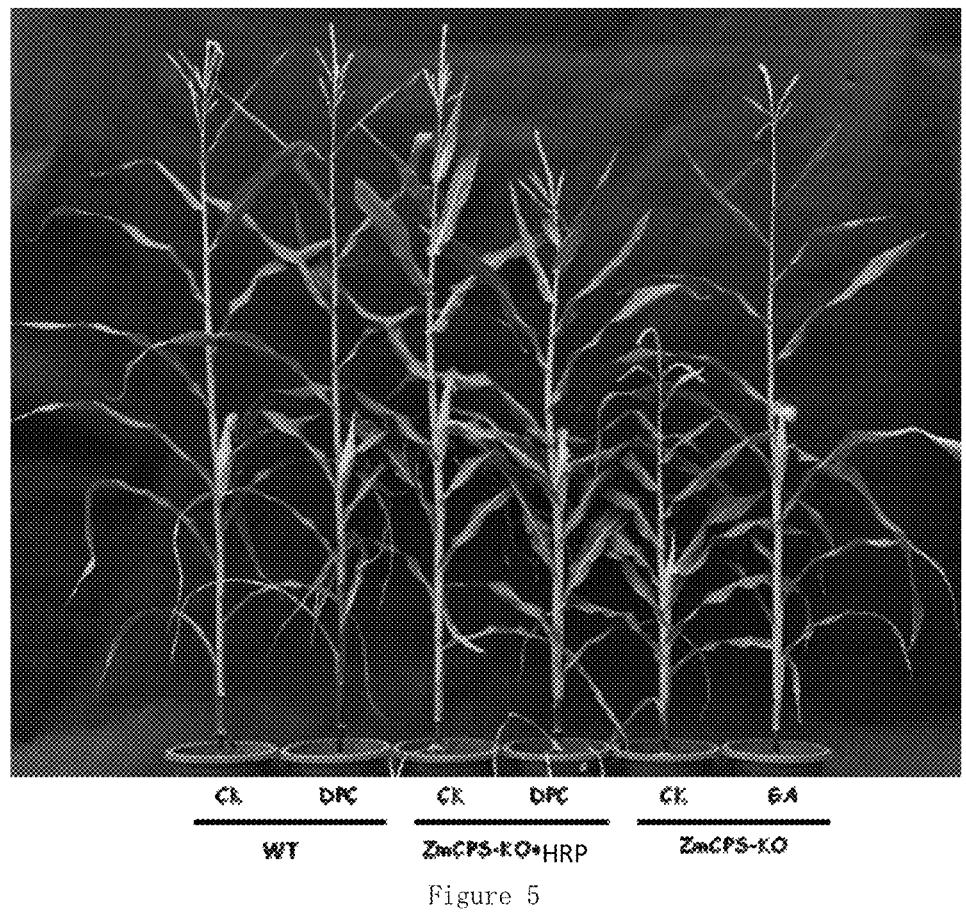
FIG. 5 is a sensitivity analysis of transgenic zmcps-ko plants with the HRP to DPC.

The results indicated that WT was insensitive to DPC, whereas the complementary plant became sensitive to DPC (FIG. 5, as shown in the results of line No. 443). From Table 4, there was no difference in the plant height between the transgenic Zmcps-ko line and the wild type (B73) under normal conditions, but DPC treatment significantly reduced the plant height and ear position of the transgenic line, but the wild type was insensitive to DPC.

TABLE 4

Regulation of DPC to the plant type of the transgenic zmcps-ko line with the HRP

| Line No. | Phenotype at the seedling stage | DPC treatment | Plant height at 2 weeks after treatment | Plant height at tasseling stage | Ear height |
| --- | --- | --- | --- | --- | --- |
| 443 | Normal plant height | DPC | 128.9 | 187.9 | 80.0 |
|  | Normal plant height | CK | 144.2 | 204.4 | 93.5 |
| 614 | Normal plant height | DPC | 133.2 | 197.9 | 80.5 |
|  | Normal plant height | CK | 141.9 | 210.5 | 90.5 |
| 623 | Normal plant height | DPC | 133.5 | 182.8 | 75.2 |
|  | Normal plant height | CK | 139.2 | 186.7 | 84.3 |
| B73 | Normal plant height | DPC | 151 | 207.5 | 91.3 |
|  | Normal plant height | CK | 149.8 | 209.4 | 90.8 |

INDUSTRIAL APPLICATION

The experiments prove that the method for increasing the sensitivity of a plant to a gibberellin inhibitor of the present invention can improve the sensitivity of plants to gibberellin inhibitors. The plant height-related protein HRP and DPC in the method for increasing the sensitivity of a plant to a gibberellin inhibitor of the present invention can regulate the plant height of *Arabidopsis thaliana*, and the plant height of transgenic *Arabidopsis thaliana* decreases with increasing DPC concentration. The plant height reduction rate of the DPC-treated HRP::ga1-1 is much higher than the ZmCPS::ga1-1, pSuper1300::ga1-1 and ga1-1 treated with the corresponding DPC concentration; the plant height reduction rate of the 30 mg/L DPC-treated HRP::ga1-1 is 2.49 times that of the ga1-1; the plant height reduction rate of the 500 mg/L DPC-treated HRP::ga1-1 is 3.47 times that of the ga1-1. The plant height reduction rate of the DPC-treated HRP::ga1-5 is much higher than the ZmCPS::ga1-1, pSuper1300::ga1-5 and ga1-5 treated with the corresponding DPC concentration; the plant height reduction rate of the 30 mg/L DPC-treated HRP::ga1-5 is 4.68 times that of the ga1-5; the plant height reduction rate of the 500 mg/L DPC-treated HRP::ga1-5 is 6.66 times that of the ga1-5.

The experiments prove that the plant height-related protein HRP of the present invention can increase the plant height of *Arabidopsis thaliana*: the plant heights of the untreated HRP::ga1-1, 30 mg/L DPC-treated HRP::ga1-1 and 500 mg/L DPC-treated HRP::ga1-1 were 3.54 times, 2.71 times and 1.71 times that of the correspondingly treated ga1-1, respectively; the plant heights of the untreated HRP::ga1-5, 30 mg/L DPC-treated HRP::ga1-5 and 500 mg/L DPC-treated HRP::ga1-5 were 2.26 times, 1.65 times and 1.00 times that of the correspondingly treated ga1-5, respectively.

The experiments prove that the method for increasing the sensitivity of a plant to a gibberellin inhibitor of the present invention can be used to increase the sensitivity of plants to gibberellin inhibitors, and the plant height of plants can be regulated by the plant height-related protein HRP of the present invention.

The invention claimed is:

1. A method for increasing the sensitivity of a plant to a gibberellin inhibitor, the method comprising: introducing a gene encoding a height-related protein (HRP) from *Gossypium arboreum* into a recipient plant to obtain a transgenic plant; wherein the transgenic plant has increased sensitivity to the gibberellin inhibitor compared to the recipient plant; wherein the plant is a dicotyledon or a monocotyledon; and wherein the height-related protein (HRP) is:

a) a protein having the amino acid sequence of positions 1-821 of SEQ ID NO: 1;

b) a protein having the amino acid sequence of SEQ ID NO:1; or c) a fusion protein obtained by attaching tag(s) to the N-terminus or/and C-terminus of the protein of a) or b).

2. The method of claim 1, further comprising knocking out the CPS (ent-copalyl diphosphate synthase) gene in the recipient plant when the recipient plant is a monocotyledon.

3. The method of claim 1, wherein the gene encoding the HRP protein is:
   i) a cDNA molecule or DNA molecule having the nucleotide sequence of positions 1-2463 of SEQ ID NO: 2;
   ii) a cDNA molecule or DNA molecule having the nucleotide sequence of SEQ ID NO: 2.

4. The method of claim 1, wherein the gibberellin inhibitor is a gibberellin synthesis inhibitor.

5. The method of claim 1, wherein the dicotyledon is *Arabidopsis thaliana*, and the monocotyledon is maize.

6. The method of claim 3, wherein the encoding sequence is the DNA molecule of SEQ ID NO: 2.

7. A method for cultivating a plant having an increased plant height, the method comprising: introducing a gene encoding a height-related protein (HRP) from *Gossypium arboreum* into a recipient plant to obtain a transgenic plant; wherein the transgenic plant has increased plant height compared to the recipient plant; wherein the transgenic plant is a dicotyledon or a monocotyledon; and wherein the height-related protein (HRP) is:
   a) a protein having the amino acid sequence of positions 1-821 of SEQ ID NO: 1;
   b) a protein having the amino acid sequence of SEQ ID NO:1; or
   c) a fusion protein obtained by attaching tag(s) to the N-terminus or/and C-terminus of the protein of a) or b).

8. The method of claim 2, wherein the CPS gene comprises SEQ ID NO: 4.

9. A transgenic plant or part thereof with increased sensitivity to a gibberellin inhibitor, wherein the transgenic plant is obtained by a method comprising: introducing a gene encoding a height-related protein (HRP) from *Gossypium arboreum* into the recipient plant to obtain the transgenic plant; and for a monocotyledon recipient plant, knocking out the CPS (ent-copalyl diphosphate synthase) gene in the recipient plant; wherein the transgenic plant has increased sensitivity to the gibberellin inhibitor compared to the recipient plant; and wherein the height-related protein (HRP) is:
   a) a protein having the amino acid sequence of positions 1-821 of SEQ ID NO: 1;
   b) a protein having the amino acid sequence of SEQ ID NO:1; or
   c) a fusion protein obtained by attaching tag(s) to the N-terminus or/and C-terminus of the protein of a) or b).

10. The plant or plant part thereof according to claim 9, wherein the plant part comprises at least one of the group consisting of cells, tissues, organs and reproductive materials.

11. The plant or plant part thereof according to claim 10, wherein the organs comprise at least one of the group consisting of seeds, leaves, fruits, stems, flowers and roots.

12. The plant or plant part thereof according to claim 10, wherein the reproductive materials comprise at least one of the group consisting of pollen, ovary, ovule, germ, endosperm, egg cell, incise, root, root tip, hypocotyl, cotyledons, stem, leaf, flower, anther, seed, meristematic cell, protoplast, and cell tissue culture.

13. The plant or plant part thereof according to claim 9, wherein the gibberellin inhibitor is a gibberellin synthesis inhibitor.

14. The plant or plant part thereof according to claim 9, wherein the plant is selected from the group consisting of *Arabidopsis thaliana* and maize.

\* \* \* \* \*